United States Patent
Leysieffer et al.

(10) Patent No.: US 6,565,503 B2
(45) Date of Patent: May 20, 2003

(54) AT LEAST PARTIALLY IMPLANTABLE SYSTEM FOR REHABILITATION OF HEARING DISORDER

(75) Inventors: Hans Leysieffer, Taufkirchen (DE); Hans Peter Zenner, Tübingen (DE); Joachim W. Baumann, Markt Schwaben (DE)

(73) Assignee: Cochlear Limited, Lane Cove (AU)

( * ) Notice: Subject to any disclaimer, the term of this patent is extended or adjusted under 35 U.S.C. 154(b) by 0 days.

(21) Appl. No.: 09/833,643

(22) Filed: Apr. 13, 2001

(65) Prior Publication Data

US 2001/0049466 A1 Dec. 6, 2001

(30) Foreign Application Priority Data

Apr. 13, 2000 (DE) .......................... 100 18 360

(51) Int. Cl.[7] .............................................. H04R 25/00
(52) U.S. Cl. ............................ 600/25; 600/379; 607/57
(58) Field of Search ...................... 600/25, 379; 607/55, 607/56, 57

(56) References Cited

U.S. PATENT DOCUMENTS

| | | |
|---|---|---|
| 3,557,775 A | 1/1971 | Mahoney |
| 3,712,962 A | 1/1973 | Epley |
| 3,764,748 A | 10/1973 | Branch et al. |
| 4,352,960 A | 10/1982 | Dormer et al. |
| 4,441,210 A | 4/1984 | Hochmair et al. |

(List continued on next page.)

FOREIGN PATENT DOCUMENTS

| | | |
|---|---|---|
| DE | 296 16 956 | 2/1997 |
| EP | 0 190 836 | 8/1986 |
| EP | 0 200 321 | 11/1986 |
| EP | 0 263 254 | 4/1988 |
| EP | 0 400 630 | 12/1990 |
| EP | 0 499 940 | 8/1992 |
| EP | 0 537 385 | 4/1993 |
| EP | 0 823 188 | 2/1997 |
| EP | 0 831 673 | 3/1998 |
| WO | 90/07251 | 6/1990 |
| WO | 99/03146 | 1/1999 |

OTHER PUBLICATIONS

E.W. LePage et al., "Non–Linear Mechanaical Behavior of the Basilar Membrane in the Basal Turn of the Guinea Pig Cochlea", pp. 183–189, 1980, Hearing Research 2.

M. Fink, "Time–Reversed Acoustics", pp. 67–73, 1999, Scientific American.

(List continued on next page.)

*Primary Examiner*—David A. Scherbel
*Assistant Examiner*—Frederick C. Nicolas
(74) *Attorney, Agent, or Firm*—Nixon Peabody LLP; David S. Safran

(57) ABSTRACT

An at least partially implantable system for rehabilitation of a hearing disorder with at least one acoustic sensor (microphone) for picking up an acoustic sensor signal and converting the acoustic sensor signal into corresponding electrical signals, an electronic signal processing unit for audio signal processing and amplification, an electrical power supply unit which supplies individual components of the system with energy, and an output-side actuator stimulation arrangement, the actuator stimulation arrangement has a dual intracochlear arrangement in combination with a stimulator arrangement with at least one stimulator element for at least indirect mechanical stimulation of a damaged inner ear and one electrically acting stimulation electrode arrangement with at least one cochlear implant electrode for electrical stimulation of the inner ear.

76 Claims, 10 Drawing Sheets

U.S. PATENT DOCUMENTS

| | | | |
|---|---|---|---|
| 4,850,962 A * | 7/1989 | Schaefer | 600/25 |
| 4,988,333 A | 1/1991 | Engebretson et al. | |
| 5,015,224 A | 5/1991 | Maniglia | |
| 5,015,225 A | 5/1991 | Hough et al. | |
| 5,061,282 A * | 10/1991 | Jacobs | 623/10 |
| 5,070,535 A | 12/1991 | Hochmair et al. | |
| 5,095,904 A | 3/1992 | Seligman et al. | |
| 5,113,859 A | 5/1992 | Funke | |
| 5,271,397 A | 12/1993 | Seligman et al. | |
| 5,279,292 A | 1/1994 | Baumann et al. | |
| 5,360,388 A | 11/1994 | Spindel et al. | |
| 5,411,467 A | 5/1995 | Hortmann et al. | |
| 5,545,219 A | 8/1996 | Kuzma | |
| 5,578,084 A | 11/1996 | Kuzma et al. | |
| 5,597,380 A | 1/1997 | McDermott et al. | |
| 5,601,617 A | 2/1997 | Loeb et al. | |
| 5,603,726 A | 2/1997 | Schulman et al. | |
| 5,624,376 A | 4/1997 | Ball et al. | |
| 5,626,629 A | 5/1997 | Faltys et al. | |
| 5,690,693 A * | 11/1997 | Wang et al. | 607/61 |
| 5,772,575 A | 6/1998 | Lesinski et al. | |
| 5,776,179 A * | 7/1998 | Ren et al. | 607/137 |
| 5,782,744 A * | 7/1998 | Money | 600/25 |
| 5,795,287 A | 8/1998 | Ball et al. | |
| 5,800,475 A | 9/1998 | Jules | |
| 5,814,095 A | 9/1998 | Müller et al. | |
| 5,951,601 A | 9/1999 | Lesinski et al. | |
| 5,957,958 A | 9/1999 | Schulman et al. | |
| 5,977,689 A | 11/1999 | Neukermans | |
| 5,984,859 A | 11/1999 | Lesinski | |
| 5,997,466 A | 12/1999 | Adams et al. | |
| 5,999,632 A | 12/1999 | Leysieffer et al. | |
| 6,005,955 A | 12/1999 | Kroll et al. | |
| 6,010,532 A * | 1/2000 | Kroll et al. | 623/10 |
| 6,038,484 A | 3/2000 | Kuzma | |
| 6,067,474 A * | 5/2000 | Schulman et al. | 607/57 |
| 6,123,660 A | 9/2000 | Leysieffer | |
| 6,131,581 A | 10/2000 | Leysieffer et al. | |
| 6,157,861 A * | 12/2000 | Faltys et al. | 607/57 |
| 6,161,046 A * | 12/2000 | Maniglia et al. | 607/57 |
| 6,171,229 B1 * | 1/2001 | Kroll et al. | 600/25 |
| 6,178,353 B1 * | 1/2001 | Griffith et al. | 607/61 |
| 6,198,971 B1 | 3/2001 | Leysieffer | |
| 6,227,204 B1 | 5/2001 | Baumann et al. | |
| 6,235,056 B1 * | 5/2001 | Kennedy | 623/10 |
| 6,251,062 B1 | 6/2001 | Leysieffer | |
| 6,259,951 B1 * | 7/2001 | Kuzma et al. | 607/57 |
| 6,264,603 B1 * | 7/2001 | Kennedy | 600/25 |
| 6,277,148 B1 * | 8/2001 | Dormer | 623/10 |
| 6,342,035 B1 * | 1/2002 | Kroll et al. | 600/25 |
| 6,358,281 B1 * | 3/2002 | Berrang et al. | 623/10 |
| 6,394,947 B1 * | 5/2002 | Leysieffer | 600/25 |
| 6,411,855 B1 * | 6/2002 | Peeters et al. | 607/57 |
| 6,261,224 B1 * | 7/2002 | Adams et al. | 600/25 |
| 6,421,569 B1 * | 7/2002 | Treaba et al. | 607/137 |
| 6,428,484 B1 * | 8/2002 | Battmer et al. | 600/554 |
| 2001/0053872 A1 * | 12/2001 | Zilberman et al. | 600/25 |

OTHER PUBLICATIONS

H.P. Zenner, "Physiology, Biochemistry, Cell and Neurobiology", pp. 20–23 and 107–108, 1994, Hören, Georg Thieme Verlag Stuttgart–New York.

H.P. Zenner et al., "Active Electronic Hearing Implants for Patients with Conductive and Sensorineural Hearing Loss—a New Era of Ear Surgery", pp. 749–757, 1997, HNO vol. 45.

H.P. Zenner et al., "First Implantations of a Totally Implantable Electronic Hearing System for Sensorineural Hearing Loss", pp. 844–852, 1998, HNO vol. 46.

H. Leysieffer et al., "A Totally Implantable Hearing Device for the Treatment of Sensorineural Hearing Loss", pp. 853–863, 1998, TICA LZ 3001, HNO vol. 46.

H. Knör, Tinnitus Retraining Therapy and Hearing Acoustics, pp. 26–27, Feb. 1997, Journal Hörakustik.

S. Ruh et al., "Cochlear Implant for Patients with Residual Hearing", pp. 347–350, 1997, Laryngo–Rhino–Otol. 76.

H.P. Zenner et al., "Totally Implantable Hearing Device for Sensorineural Hearing Loss", p. 1751, Nov. 28, 1998, The Lancet, vol. 352, No. 9142.

E. Lehnhardt, "Intracochlear Placement of Cochlear Implant Electrodes in Soft Surgery Technique", pp. 356–359, 1993, HNO vol. 41.

N. Yanagihara et al., "Implantable Hearing Aid", pp. 869–872, Aug. 1987, Arch Otolaryngal Head Neck Surgery–vol. 113.

J. Mülle–Deile et al., "Cochlear Implant Supply for Non–Deaf Patients?", pp. 136–143, 1998, Laryngo–Rhino–Otol.

J. Suzuki et al., "Implantation of Partially Implantable Middle Ear Implant and the Indication", pp. 160–166, Karger Basel, p. 1988, Advances in Audiology.

* cited by examiner

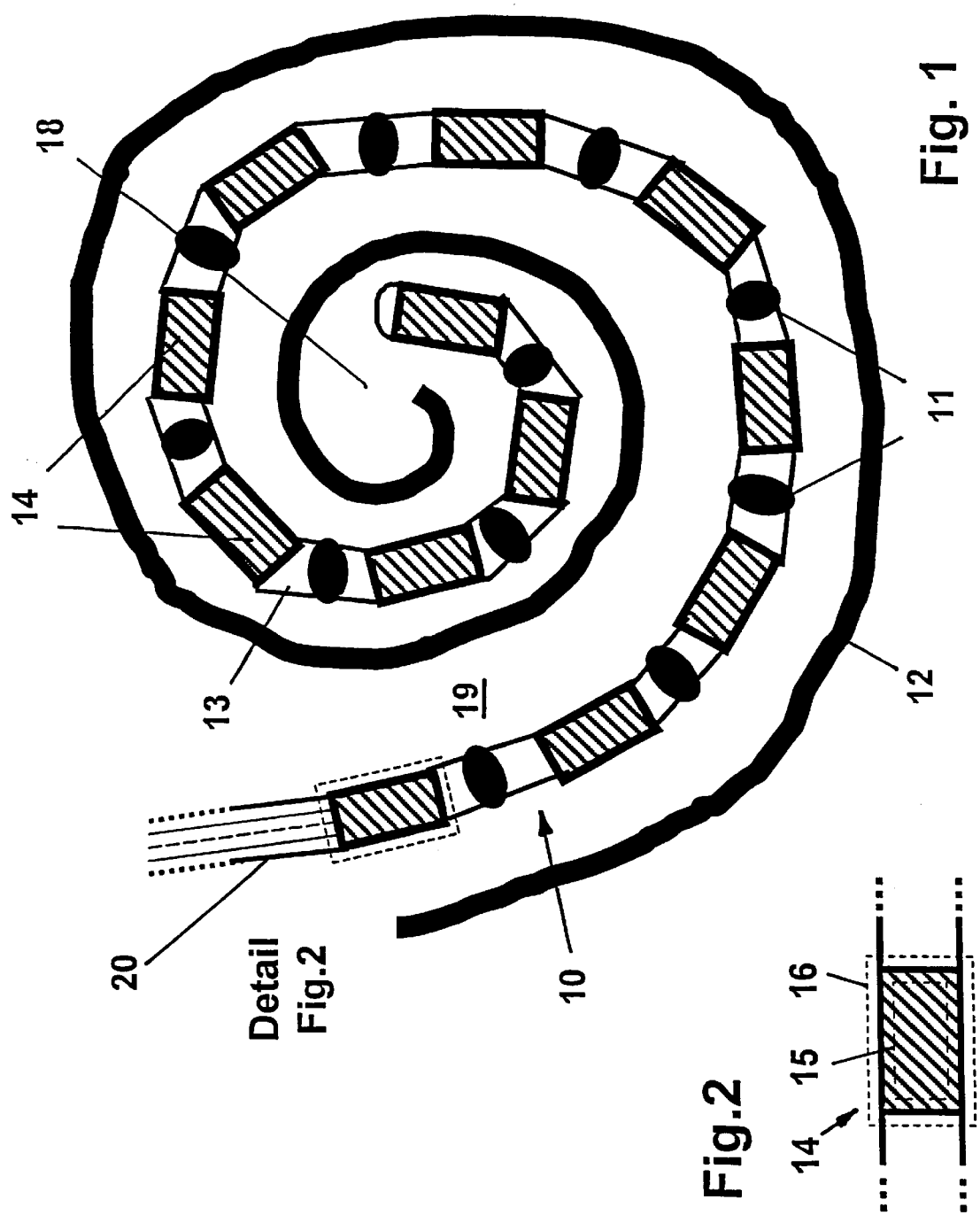

AT LEAST PARTIALLY IMPLANTABLE SYSTEM FOR REHABILITATION OF HEARING DISORDER

SUMMARY OF THE INVENTION

1. Field of the Invention

This invention relates to an at least partially implantable system for rehabilitation of a hearing disorder which comprises at least one sensor (microphone) for picking up an acoustic signal and converting the acoustic signal into the corresponding electrical signals, an electronic signal processing unit for audio signal processing and amplification, an electrical power supply unit which supplies individual components of the system with current, and an output-side actoric stimulation arrangement.

2. Description of Related Art

The expression "hearing disorder" is defined here as inner ear damage, combined inner ear and middle ear damage, and a temporary or permanent noise impression (tinnitus).

In recent years rehabilitation of sensorineural hearing disorders with partially implantable electronic systems has acquired major importance. In particular, this applies to the group of patients in which hearing has completely failed due to accident, illness or other effects or in which hearing is congenitally non-functional. If, in these cases, only the inner ear (cochlea), and not the neural auditory path which leads to the brain, is affected, the remaining auditory nerve can be stimulated with electrical stimulation signals. Thus, a hearing impression can be produced which can lead to speech comprehension. In these so-called cochlear implants (CI), an array of stimulation electrodes, which is controlled by an electronic system (electronic module) is inserted into the cochlea. This electronic module is encapsulated with a hermetical, biocompatible seal and is surgically embedded in the bony area behind the ear (mastoid). The electronic system contains essentially only decoder and driver circuits for the stimulation electrodes. Acoustic sound reception, conversion of this acoustic signal into electrical signals and their further processing, always takes place externally in a so-called speech processor which is worn outside on the body. The speech processor converts the preprocessed signals into a high frequency carrier signal which, via inductive coupling, is transmitted through the closed skin (transcutaneously) to the implant. The sound-receiving microphone is always located outside of the body and, in most applications, in a housing of a behind-the-ear hearing aid worn on the external ear. The microphone is connected to the speech processor by a cable. Such cochlear implant systems, their components, and the principles of transcutaneous signal transmission are described, by way of example, in published European Patent Application EP 0 200 321 A2 and in U.S. Pat. Nos. 5,070,535, 4,441,210, 5,626,629, 5,545,219, 5,578,084, 5,800,475, 5,957,958 and 6,038,484. Processes of speech processing and coding in cochlear implants are described for example in published European Patent Application EP 0 823 188 A1, in European Patent 0 190 836 A1 and in U.S. Pat. Nos. 5,597,380, 5,271,397, 5,095,904, 5,601,617 and 5,603,726.

In addition to rehabilitation of congenitally deaf persons and those who have lost their hearing using cochlear implants, for some time there have been approaches to offer better rehabilitation than with conventional hearing aids to patients with a sensorineural hearing disorder which cannot be surgically corrected by using partially or totally implantable hearing aids. The principle arises, in most embodiments, in stimulating an ossicle of the middle ear or, directly, the inner ear via mechanical or hydromechanical stimulation and not via the amplified acoustic signal of a conventional hearing aid in which the amplified acoustic signal is supplied to the external auditory canal. The actuator stimulus of these electromechanical systems is accomplished with different physical transducer principles such as, for example, by electromagnetic and piezoelectric systems. The advantage of these devices is seen mainly in the sound quality which is improved compared to conventional hearing aids, and, for totally implanted systems, in the fact that the hearing prosthesis is not visible.

Such partially and fully implantable electromechanical hearing aids are described, for example, by Yanigahara et al. "Implantable Hearing Aid", Arch Otolaryngol Head Neck Surg-Vol 113, 1987, pp. 869–872; Suzuki et al. "Implantation of Partially Implantable Middle Ear Implant and the Indication", Advances in Audiology, Vol. 4, 160–166, Karger Basel, 1988; H. P. Zenner et al. "First implantations of a totally implantable electronic hearing system for sensorineural hearing loss", in HNO Vol. 46, 1998, pp. 844–852; H. Leysieffer et al. "A totally implantable hearing device for the treatment of sensorineural hearing loss: TICA LZ 3001", HNO Vol. 46, 1998, pp. 853–863; H. P. Zenner et al. "Active electronic hearing implants for patients with conductive and sensorineural hearing loss—a new era of ear surgery", HNO 45: 749–774; H. P. Zenner et al. "Totally implantable hearing device for sensorineural hearing loss", The Lancet Vol. 352, No. 9142, page 1751; and are described in numerous patent documents among others in published European Patent Applications EP 0 263 254 A1, EP 0 400 630 A1, and EP 0 499 940 A1, and in U.S. Pat. Nos. 3,557,775, 3,712,962, 3,764,748, 5,411,467, 4,352,960, 4,988,333, 5,015,224, 5,015,225, 5,360,388, 5,772,575, 5,814,095, 5,951,601, 5,977,689 and 5,984,859. Here, the insertion of an electromechanical transducer through an opening in the promontory for direct fluid stimulation in the inner ear is described in U.S. Pat. Nos. 5,772,575, 5,951, 601, 5,977,689 and 5,984,859.

Many patients with inner ear damage also suffer from temporary or permanent noise impressions (tinnitus) which cannot be surgically corrected and for which, to date, there are no approved drug treatments. Therefore, so-called tinnitus maskers (International Patent Application Publication WO-A 90/07251, published European Patent Application EP 0 537 385 A1, German Utility Model No. 296 16 956) are known. These devices are small, battery-driven devices which are worn like a hearing aid behind or in the ear and which, by means of artificial sounds which are emitted, for example, via a hearing aid speaker into the auditory canal, psychoacoustically mask the tinnitus and thus reduce the disturbing noise impression, if possible, to below the threshold of perception. The artificial sounds are often narrowband noise (for example, third-band noise). The spectral position and the loudness level of the noise can be adjusted via a programming device to enable adaptation to the individual tinnitus situation as optimally as possible. In addition, the so-called retraining method has been developed recently in which, by combination of a mental training program and presentation of broadband sound (noise) near the auditory threshold, the perceptibility of the tinnitus in quiet conditions is likewise supposed to be largely suppressed (H. Knoer "Tinnitus retraining therapy and hearing acoustics" journal "Hoerakustik" 2/97, pages 26 and 27). These devices are also called "noisers".

In the two aforementioned methods for hardware treatment of tinnitus, hearing aid-like, technical devices must be carried visibly outside on the body in the area of the ear; these devices stigmatize the wearer and, therefore, are not willingly worn.

U.S. Pat. No. 5,795,287 describes an implantable tinnitus masker with direct drive of the middle ear, for example, via an electromechanical transducer coupled to the ossicular chain. This directly coupled transducer can preferably be a so-called "Floating Mass Transducer" (FMT). This FMT corresponds to the transducer for implantable hearing aids which is described in U.S. Pat. No. 5,624,376.

In commonly owned co-pending U.S. patent applications Ser. Nos. 09/372,172 and 09/468,860, which are hereby incorporated by reference, implantable systems for treatment of tinnitus by masking and/or noiser functions are described, in which the signal-processing electronic path of a partially or totally implantable hearing system is supplemented by corresponding electronic modules such that the signals necessary for tinnitus masking or noiser functions can be fed into the signal processing path of the hearing aid function and the pertinent signal parameters can be individually adapted by further electronic measures to the pathological requirements. This adaptability can be accomplished by storing or programming the necessary setting data of the signal generation and feed electronics by using hardware and software in the same physical and logic data storage area of the implant system, and by controlling the feed of the masker or noiser signal into the audio path of the hearing implant via the corresponding electronic actuators.

Depending on the desired function, implantable rehabilitation devices of the aforementioned type consist of several functional units, especially: (1) a sensor (microphone) which converts the incident airborne sound into an electrical signal; (2) an electronic signal processing, amplification and implant control unit; (3) an implantable electromechanical or electroacoustic transducer which converts the amplified and preprocessed sensor signals into mechanical or acoustic vibrations and sends them via suitable coupling mechanisms to the damaged middle and/or inner ear, or, in the case of cochlear implants a cochlear stimulation electrode; and (4) an electric power supply system which supplies the aforementioned modules. Furthermore, there can be an external unit which makes available electrical recharging energy to the implant when the implant-side power supply unit contains a rechargeable (secondary) battery. Especially advantageous devices and processes for charging rechargeable implant batteries are described in commonly owned co-pending U.S. patent application Ser. No. 09/311,566 and in commonly owned U.S. Pat. No. 5,279,292, which are hereby incorporated by reference. Preferably, there can also be a telemetry unit with which patient-specific, audiological data can be wirelessly transmitted bidirectionally or programmed in the implant and thus permanently stored, as was described by Leysieffer et al. in HNO Vol. 46, 1998, pp. 853–863.

Basically, in all these at least partially implantable systems, the (audio) signal processing or signal generation and the implant control modules, such as, for example, a controlled battery recharging system or a telemetry system for bidirectional transmission of, for example, variable, patient-specific parameters are accomplished on the implant-side by permanently fixed hardware units. This also applies when digital signal processors, microcontrollers or microprocessors are used for signal processing or generation or for implant management, regardless of whether the signal processors are built as so-called "hardwired logic", i.e., in "hardwired" logic architecture, or whether their operating programs are stored in the read-only memory areas (for example, ROM) of the corresponding processors. These programs, which are provided and are necessary for basic operation of the implant and for the intended functions, are hereinafter called the operating program or the operating software. In the known implant systems, this operating software is placed in the system during production, for example, by mask programming of processor storage areas and can no longer be changed after implantation.

In contrast thereto, patient-specific data such as, for example, audiological adaptation data or variable implant system parameters (for example, a variable in one of the software programs for control of battery recharging mentioned above) are herein called operating parameters. In known totally implantable implant systems, after implantation, these operating parameters can be transmitted transcutaneously, i.e., wirelessly through the closed skin, to the implant and thus can be changed.

The above described at least partially implantable hearing systems for rehabilitation of inner ear damage which are based on an output-side electromechanical transducer, differ from conventional hearing aids essentially only in that the output-side acoustic stimulus (i.e., an amplified acoustic signal in front of the eardrum) is replaced by an amplified mechanical stimulus of the middle ear or inner ear. The acoustic stimulus of a conventional hearing aid ultimately leads to vibratory, i.e., mechanical, stimulation of the inner ear, via mechanical stimulation of the eardrum and the subsequent middle ear. The requirements for effective audio signal preprocessing are fundamentally similar or the same. Furthermore, in both embodiments on the output side a localized vibratory stimulus is ultimately routed to the damaged inner ear (for example, an amplified mechanical vibration of the stapes in the oval window of the inner ear).

Basically, in this routinely used rehabilitation of inner ear damage by active hearing systems (regardless of whether the rehabilitation is by an external acoustic stimulus or by an implanted electromechanical stimulus), at present there is a major drawback which is described below in summary for understanding of this invention: most cases of sensorineural deafness are based on more or less pronounced damage of the outer hair cells in the inner ear. These outer hair cells, which in large number are located in the organ of Corti along the basilar membrane, form part of the so-called cochlear amplifier which, depending on local excitation of the basilar membrane as a result of traveling wave formation, actively mechanically de-attenuates this local stimulation range at low levels and thus small traveling wave amplitudes, which leads to an increase in sensitivity. This active amplification is based on a very complex, efferently controlled process which is not described here. It is furthermore assumed that at very high levels of inner ear stimulation as a result of the high loudness, this effect is reversed in its action and thus locally reduces and actively attenuates the traveling wave amplitude. These nonlinear characteristics of the cochlear amplifier, which is located along the organ or Corti in several hundred functional units with locally limited action, are of decisive importance for the function of the healthy inner ear. In partial or total failure of the outer hair cells, in addition to a loss of sensitivity which leads to a rise in the hearing threshold, other disadvantages arise: the described active de-attenuation of the basilar membrane leads to high Q-factors of the envelopes of the traveling waves (tuning curves) which are essentially responsible for the frequency differentiation capacity (tone pitch differences). If this high quality is lacking due to failure or partial damage of the outer hair cells, the affected individual can perceive tone pitch differences much more poorly. The rise of the hearing threshold leads, moreover, to a reduction of the dynamic range since the upper sensory boundary (discomfort threshold) in labyrinthine deafness does not rise at the same time. This reduction of dynamics results in an increased perception of loudness which is called positive recruitment. The described effects, which are caused by damage or failure of the outer hair cells, lead, in the overall effect for the affected individual, to a reduction in speech comprehension, especially in a noisy environment (summary description in Zenner, H. P.: *Hearing*, Georg Thieme Verlag Stuttgart, New York, 1994, pages 20–23, 107 and 108, and LePage, E. W., Johnstone, M. B.: "Non-linear mechanical behavior of the basilar membrane in the basal turn of the guinea pig cochlea." Hearing Research 2 (1980), pp. 183–189).

An important consequence of this described mechanism is that, as indicated above, both in conventional acoustic hearing aids and also in partially or fully implantable hearing systems, the important functions of the damaged outer hair cells and thus of the cochlear amplifier cannot be replaced or at least partially restored. U.S. Pat. No. 6,123,660 discloses a converter arrangement for partially or fully implantable hearing aids for direct mechanical excitation of the middle ear or inner ear, which is provided with a piezoelectric converter element and also with an electromagnetic converter which are accommodated in a common housing and the two can be coupled via the same coupling element to the middle ear ossicle or directly to the inner ear. Furthermore, implantable hearing systems are known (U.S. Pat. No. 5,997,466, 6,005,955) which work with two or more output-side electromechanical converters in one or locally separate arrangements. These embodiments are, however, uniquely described in that a system design with more than one converter enables a linear superposition of the deflection frequency responses of the individual converters which, as a result, allows an output-side excitation form of the cochlea which is adjustable or programmable depending specifically on frequency or spectrally optimized as much as possible and thus will lead to a spectrally balanced and sufficient loudness impression of the implant system. Rehabilitation of the cochlear amplifier with the aforementioned features is, however, not possible by these embodiments or described signal preprocessing methods.

In cochlear implants (CI), solely electrical stimulation signals are now used as the actuator stimuli. After implantation of a CI in completely deaf patients, training is generally necessary for rehabilitation of hearing, since the artificial stimuli must be learned, because the artificial stimuli do not fundamentally correspond to the biologically proper form of stimulation of the inner ear. Conversely, this rehabilitation phase is omitted after implantation of an electromechanical hearing system in those with hearing difficulties since the mechanical form of stimulation is biologically suitable, as described above, and since the mechanical form of stimulation ultimately largely corresponds with a hearing aid at least with respect to the basic function, i.e., the stimulation at the input of the inner ear is of a vibratory nature.

For the aforementioned reasons, implantable electromechanical systems cannot be employed for hearing disorders which approach deafness. Here, cochlear implants with purely electrical stimulation of the inner ear may be considered which of course do not promise sound quality which for example would enable acceptable music transmission, but which rather are primarily designed for acquiring or restoring sufficient speech comprehension, as much as possible without lip reading. As a result of the electrical stimulation, as described, hearing losses which extend to complete deafness are possible in a spectrally wide audiological range.

Recently it has become scientifically known from CI implantations that even for incomplete deafness cochlear implants (CIs) can be successfully used when sufficient speech discrimination can no longer be achieved with a conventional hearing aid. Interestingly it was demonstrated that the important inner ear structures which enable residual acoustic hearing capacity can be maintained in part or largely stably over time when a CI electrode is inserted into the cochlea (S. Ruh et al.: "Cochlear implant for patients with residual hearing", Laryngo-Rhino-Otol. 76 (1997) pp. 347–350; J. Mueller-Deile et al.: "Cochlear implant supply for non-deaf patients?" Laryngo-Rhino-Otol. 77 (1998) pp. 136–143; E. Lehnhardt: "Intracochlear placement of cochlear implant electrodes in soft surgery technique", HNO 41 (1993), pp. 356–359). In the foreseeable future it certainly will be possible, in case of residual hearing capacity, to clinically place CI electrodes intracochlearly in a manner such that the remaining inner ear structures can be preserved over the long term and thus can continue to be stimulated in a biologically proper manner, i.e., vibrationally, and lead to a usable hearing impression.

SUMMARY OF THE INVENTION

The object of the invention is to devise an at least partially implantable system for rehabilitation of a hearing disorder which can be matched especially effectively and flexibly to the individual pathological and audiological situation of the respective patient.

This object is achieved in that, in an at least partially implantable system for rehabilitation of a hearing disorder which comprises at least one sensor (microphone) for picking up an acoustic signal and converting the acoustic signal into corresponding electrical signals, an electronic signal processing unit for audio signal processing and amplification, an electrical power supply unit which supplies individual components of the system with current, and an output-side actuator stimulation arrangement, as the actuator stimulation arrangement there is a dual intracochlear arrangement which in combination has a stimulator arrangement with at least one stimulator element for at least indirect mechanical stimulation of the inner ear and an electrically acting stimulation electrode arrangement with at least one cochlear implant electrode for electrical stimulation of the inner ear.

With the system both stimulation methods, i.e., the use of mechanical and electrical stimulation, can be used in a single implant system and can be applied patient-specifically depending on the individual audiological situation ("dual" hearing implant). Direct stimulation of the cochlea prevents or largely reduces the occurrence of feedback, i.e., coupling of the output signal into the sensor (microphone) because the ossicle chain and thus the eardrum are not excited to vibrations or at least are to a reduced degree. This is especially advantageous when an acoustic sensor (microphone function) is applied in the immediate vicinity of the eardrum, as is known from U.S. Pat. Nos. 5,814,095 and 5,999,632. Therefore, overall with this implant system the use of a combined "dual" output-side converter array circumvents or at least reduces the indicated drawbacks of a purely electromechanically acting hearing system and of a purely electrically acting implantable CI such that by the combined action of the two forms of stimulation and individually maximized parameter adjustment of the controlling electronic preprocessing system on the one hand an indication position as audiologically wide as possible and on the other hand in individual patients a result as optimum as possible with respect to speech discrimination, sufficient loudness in all relevant spectral ranges and high sound quality are achieved.

The stimulator arrangement can advantageously have at least one intracochlear electromechanical converter for direct mechanical stimulation of the inner ear and/or at least one intracochlear hair cell stimulating electrode for indirect mechanical stimulation of the inner ear by electrical stimulation of the outer hair cells. Preferably there is an intracochlear array with several stimulator elements for direct and/or indirect mechanical stimulation of the inner ear which can be implanted directly into the fluid-filled space of the inner ear (scala tympani or scala vestibuli) just like a cochlear implant electrode array which is provided preferably with a plurality of cochlear implant electrodes.

The hair cell stimulation electrodes intended for indirect mechanical stimulation of the inner ear are preferably made such that in the implanted state the hair cell stimulation electrodes come to rest in the immediate vicinity of the outer hair cells. Here the circumstance is used that the outer hair cells react mechanically with changes in length when the outer hair cells are artificially stimulated by electricity. These dynamic elongations are synchronous with the electrical stimulation signal up to very high frequencies which can extend to above the audiological range to be supplied. In this way, similarly to when using intracochlear electromechanical converters, electrical stimulation forms achieved on the output side for example by means of cochlear implant electrodes can be combined with mechanical cochlear stimulations because the outer hair cells are directly operated as "electromechanical converters" as takes place in a healthy, undamaged inner ear biologically by neural efferent triggering. This application is especially suitable for pathological cases in which only the outer hair cells are damaged for example by ototoxic medications, i.e., the outer hair cells can no longer perform their neural transmitter function or can only do so to a limited degree, the stereocilia which "mechanically" join the hair cells to the tectorial membrane are however undamaged or intact to such an extent that there is reliable mechanical coupling to the tectorial membrane stable over the long term.

The cochlear implant electrode(s) intended for direct electrical stimulation of the inner ear is (are), as is known in the prior art for cochlear implants, feasibly embedded in the carrier or fixed or on the carrier such that in the implanted state a portion of the surface of each stimulation electrode is in direct galvanic contact with the lymphatic fluid of the inner ear or directly with one of the neural structures to be stimulated.

There can be a common carrier for the cochlear implant electrode(s) and the electromechanical converter(s), the electromechanical converter(s) and the cochlear implant electrode(s) being arranged advantageously along the carrier alternating in one another. In this way mechanical wave propagation within the carrier between adjacent electromechanical converter elements can be damped and locally concentrated mechanical stimulation per converter can be achieved.

However, there can also be separate carriers for the cochlear implant electrode(s) and the electromechanical converter(s). In this case, the carrier for the cochlear implant electrode(s) is arranged such that in the implanted state the carrier is oriented to the inside with reference to the cochlea, in order to lie as near as possible to the neural structure (modiolus) to be stimulated.

The dual intracochlear arrangement preferably has a total diameter in the range of 0.4 mm (apical area) to 2.0 mm (basal area) and a total length between 5 mm and 50 mm. The carrier or carriers advantageously comprise a biocompatible material which is biostable in the inner ear, preferably a polymer, especially a silicone. The individual electromechanical converters can be embedded in the carrier for reasons of biocompatibility such that the individual electromechanical converters are completely surrounded by a thin layer of the carrier material.

In order to minimize mechanical wave propagation from a converter within the carrier to adjacent converters, in another embodiment of the invention between the individual output-side electromechanical converters mechanical attenuation elements are embedded in the carrier, the material of the attenuation elements for a similar cross sectional geometry to that of the carrier being preferably chosen such that to achieve high attenuation values there is a high mechanical impedance difference compared to the carrier material. As already mentioned, optionally the cochlear implant electrodes can moreover be used as attenuation elements.

The electromechanical converter(s) is (are) preferably made hermetically sealed and the electromechanical converter(s) can work fundamentally according to any known electromechanical converter principle, and can be made especially as electromagnetic, electrodynamic, piezoelectric, magnetostrictive or dielectric (capacitive) converters. When using the piezoelectric converter principle the electromechanical converter(s) is (are) advantageously made using PZT ceramic (lead zirconate titanate) or PVDF (polyvinylidene fluoride), preferably using geometrical shape transformations, especially the bimorph principle, the unimorph principle or the heteromorph principle with passive material partners such that at a given converter voltage the electromechanical converter(s) produce maximum deflection with minimum electric power consumption.

In another embodiment of the invention, several stimulator elements for at least indirect mechanical stimulation of the inner ear are arranged distributed equidistantly or at logarithmic distances according to the tonotopic frequency-location assignment along the basilar membrane of the inner ear, and in the case of a tonotopic arrangement of stimulator elements for mechanical stimulation of the inner ear 20 to 24 stimulator elements or groups of stimulator elements can lead to especially favorable results according to psychoacoustic critical bands.

The electromechanical converter(s) feasibly has (have) a transmission range from roughly 100 Hz to roughly 10 kHz and electromechanical converter(s) is (are) preferably highly tuned, i.e., the first mechanical resonant frequency is at the upper end of the desired transmission frequency range, especially at roughly 8 kHz to roughly 10 kHz. This results in that the deflection frequency response of the converters in the transmission range is largely free of resonances and for voltage impression and the use of piezoelectric converters is flat regardless of frequency. Thus there is no ripple in the transmission range.

The cochlear implant electrode(s) and/or the hair cell stimulation electrode(s) can comprise all known biocompatible metals, especially pure platinum, preferably platinum-iridium alloys (preferably 90% Pt, 10% Ir), pure gold, gold alloys, tantalum, tantalum alloys, niobium, niobium alloys and high quality steels.

The signal processing unit feasibly has a preprocessing arrangement for pre-amplification and/or filtering and for analog-digital (A/D) conversion of the acoustic sensor signals. The signal processing unit can in particular comprise anti-aliasing filters. In the presence of several acoustic sensors preferably each of the acoustic sensors is upstream of its own analog-digital converter.

In another embodiment of the invention, the signal processing unit can contain software modules which parallel to operation of the hearing aid enables masking of tinnitus. With this multichannel hearing implant system, tinnitus which can be at least peripherally localized can be masked more effectively than with known conventional tinnitus maskers.

The signal processing unit advantageously has a digital signal processor for processing the A/D-converted acoustic sensor signals which have been optionally preprocessed by means of the preprocessing arrangement and/or for generation of digital signals for tinnitus masking, at least one analog-digital converter being assigned to the actuator stimulation arrangement and preferably upstream of the stimulator element(s) for at least indirect mechanical stimulation of the inner ear and the cochlear implant electrode(s) for electrical stimulation of the inner ear its own digital-analog converter being located.

In another embodiment of the invention, the signal processing electronics contains software modules which trigger the stimulator element(s) for at least indirect mechanical stimulation of the inner ear, therefore especially the intra-cochlear electromechanical converters which directly mechanically excite the inner ear and/or the hair cell stimulation electrodes which mechanically excite the inner ear in interaction with the outer hair cells, such that the spectral, time, amplitude- and phase-referenced properties of the signals which trigger the stimulator elements are dimensioned such that a traveling wave is produced on the basilar membrane of the damaged inner ear which is as near as possible to that of healthy hearing.

The software modules can be designed to be static such that as a result of scientific findings the software modules are filed once in the program storage of the digital signal processor and remain unchanged. But then if later for example due to more recent scientific findings improved algorithms for speech signal processing are available and these improved algorithms are to be used, the entire implant or implant module which contains the corresponding signal processing unit must be replaced by a new unit with the altered operating software by invasive surgery on the patient. This surgery entails renewed medical risks for the patient and is very complex.

This problem can be solved in that, in another embodiment of the invention, a wireless, preferably PC-based telemetry means is provided for transmission of data between the implanted part of the system and an external unit, especially an external programming system, a rewritable implantable storage arrangement is assigned to the signal processor for accommodating and reproducing the operating program and at least parts of the operating program can be replaced or changed by data transmitted from the external unit via the telemetry means. In this way, after implantation of the implantable system the operating software as such can be changed or completely replaced, as is explained for otherwise known systems for rehabilitation of hearing disorders in U.S. Pat. No. 6,198,971.

In addition, the design of totally implantable systems preferably is such that, in a manner known per se, after implantation also operating parameters, i.e., patient-specific data, for example audiological adaptation data, or variable implant system parameters (for example, a variable in a software program for control of battery recharging), can be transmitted transcutaneously, i.e., wirelessly through the closed skin, to the implant and can thus be changed. In such a case the software modules are designed to be preferably dynamic, or in other words, adaptive, in order to rehabilitate the hearing disorder as optimally as possible. In particular the software modules can be designed to be adaptive, and parameter matching can be accomplished by training by the implant wearer and using other aids.

Furthermore, the signal processing electronics can contain a software module which achieves simulation of a "healthy" cochlear amplifier as optimum as possible based on an adaptive neural network. Training of this neural network can take place again by the implant wearer and/or using other external aids. Especially in the neural network for simulation of a "healthy" cochlear amplifier the principle of time-reversed acoustics (TRA) can be implemented, and triggering of the output-side electromechanical converters can take place by TRA such that locally limited areas of the cochlea are mechanically stimulated.

The storage arrangement for storage of operating parameters and the storage arrangement for holding and reproducing the operating program can be implemented as storages independent of one another; however there can also be a single storage in which both the operating parameters and also operating programs can be filed.

The storage arrangement for storage of operating parameters and the storage arrangement for storage and retrieval of the operating program can be implemented as storages independent of one another; however there can also be a single storage in which both the operating parameters and also operating programs can be filed.

This approach allows matching of the system to circumstances which can be detected only after implantation of the implantable system. Thus, for example, in an at least partially implantable hearing system for rehabilitation of a monaural or binaural inner ear disorder and of a tinnitus by mechanical stimulation of the inner ear, the sensoric (acoustic sensor or microphone) and actoric (output stimulator) biological interfaces are always dependent on anatomic, biological and neurophysiological circumstances, for example on the interindividual healing process. These interface parameters can also be individual, also especially time-variant. Thus, for example the transmission behavior of an implanted microphone can vary interindividually and individually as a result of being covered by tissue, and the transmission behavior of an electromechanical transducer which is coupled to the inner ear can vary in view of on different coupling qualities. These differences of interface parameters which cannot be eliminated or reduced in the devices known from the prior art even by replacing the implant can now be optimized by changing or improving the signal processing of the implant.

In an at least partially implantable hearing system, it can be advisable or become necessary to implement signal processing algorithms which have been improved after implantation. Especially the following should be mentioned here:

speech analysis processes (for example, optimization of a fast Fourier transform (FFT))
static or adaptive noise detection processes
static or adaptive noise suppression processes
processes for optimization of the signal to noise ratio within the system
optimized signal processing strategies in progressive hearing disorder
output level-limiting processes for protection of the patient in case of implant malfunctions or external faulty programming processes of preprocessing of several sensor (microphone) signals, especially for binaural positioning of the sensors processes for binaural processing of two or more sensor signals in binaural sensor positioning, for example optimization of spacial hearing or spacial orientation phase or group delay time optimization in binaural signal processing processes for optimized driving of the output stimulators, especially for binaural positioning of the stimulators.

Among others, the following signal processing algorithms can be implemented with this system even after implantation:

processes for feedback suppression or reduction processes for optimization of the operating behavior of the output transducer(s) (for example, optimization of the frequency response and phase response, improvement of the impulse response)

speech signal compression processes for sensorineural hearing loss signal processing methods for recruitment compensation in sensorineural hearing loss.

Furthermore, in implant systems with a secondary power supply unit, i.e., a rechargeable battery system, but also in systems with primary battery supply it can be assumed that these electrical power storages will enable longer and longer service lives and thus increasing residence times in the patients as technology advances. It can be assumed that fundamental and applied research for signal processing algorithms will make rapid progress. The necessity or the patent desire for operating software adaptation and modification will therefore presumably take place before the service life of the implanted power source expires. The system described here allows this adaptation of the operating programs of the implant even when the implant has already been implanted.

Preferably, there can furthermore be provided a buffer storage arrangement in which data transmitted from the external unit via the telemetry means can be buffered before being relayed to the signal processor. In this way the transmission process from the external unit to the implanted system can be terminated before the data transmitted via the telemetry means are relayed to the signal processor.

Furthermore, there can be provided checking logic which checks the data stored in the buffer storage arrangement before relaying the data to the signal processor. There can be provided a microprocessor module, especially a microcontroller, for control of the A/D-converters and/or the D/A converters and/or the signal processor within the implant via a data bus, preferably the checking logic and the buffer storage arrangement being implemented in the microprocessor module, and wherein also program parts or entire software modules can be transferred via the data bus and the telemetry means between the outside world, the microprocessor module and the signal processor.

An implantable storage arrangement for storing the working program for the microprocessor module is preferably assigned to the microprocessor module, and at least parts of the working program for the microprocessor module can be changed or replaced by data transmitted from the external unit via the telemetry means.

In another embodiment of the invention, at least two storage areas for storage and retrieval of at least the operating program of the signal processor may be provided. This contributes to the reliability of the system, in that due to the multiple presence of a storage area which contains the operating program(s), for example, after transmission from the exterior or when the implant is turned on, checking for the absence of faults in the software can be done.

Analogously to the above, the buffer storage arrangement can also comprise at least two storage areas for storage and retrieval of data transferred from the external unit via the telemetry means, so that after data transmission from the external unit still in the area of the buffer storage the absence of errors in the transferred data can be checked. The storage areas can be designed for example for complementary filing of the data transferred from the external unit. At least one of the storage areas of the buffer storage arrangement however can also be designed to store only part of the data transferred from the external unit, wherein in this case the absence of errors in the transferred data is checked in sections.

Furthermore, to ensure that in case of transmission errors, a new transmission process can be started, a preprogrammed read-only memory area which cannot be overwritten can be assigned to the signal processor, in which ROM area the instructions and parameters necessary for "minimum operation" of the system are stored, for example, instructions which after a "system crash" ensure at least error-free operation of the telemetry means for receiving an operating program and instructions for its storage in the control logic.

As already mentioned, the telemetry means is advantageously designed not only for reception of operating programs from the external unit but also for transfer of operating parameters between the implantable part of the system and the external unit such that on the one hand such parameters (for example the volume) can be adjusted by a physician, a hearing aid acoustics specialist or the wearer of the system himself, and on the other hand the system can also transfer the parameters to the external unit, for example to check the status of the system.

A totally implantable hearing system of the aforementioned type can have on the implant side in addition to the actoric stimulation arrangement and the signal processing unit at least one implantable acoustic sensor and a rechargeable electrical storage element, and in this case a wireless transcutaneous charging device can be provided for charging of the storage element. For a power supply there can also be provided a primary cell or another power supply unit which does not require transcutaneous recharging. This applies especially when it is considered that in the near future mainly by continuing development of processor technology a major reduction in power consumption for electronic signal processing can be expected so that for implantable hearing systems new forms of power supply will become usable in practice, for example power supply which uses the Seebeck effect, as is described in U.S. Pat. No. 6,131,581. Preferably, there is also provided a wireless remote control for control of the implant functions by the implant wearer.

In case of a partially implantable hearing system, at least one acoustic sensor, an electronic signal processing arrangement, a power supply unit and a modulator/transmitter unit are contained in an external module which can be worn outside on the body, especially on the head over the implant. The implant comprises the output-side electromechanical transducer and the intracochlear stimulation electrode array, but is passive in terms of energy and receives its operating energy and transducer control data via the modulator/transmitter unit in the external module.

The described system can be designed to be monaural or binaural for the fully implantable design as well as for the partially implantable design. A binaural system for rehabilitation of a hearing disorder of both ears has two system units which each are assigned to one of the two ears. In doing so the two system units can be essentially identical to one another. However, one of the system units can also be designed as a master unit and the other system unit as a slave unit which is controlled by the master unit. The signal processing modules of the two system units can communicate with one another in any way, especially via a wired implantable line connection or via a wireless connection, preferably a bidirectional high frequency path, a ultrasonic path coupled by bone conduction, or a data transmission path which uses the electrical conductivity of the tissue of the implant wearer such that in both system units optimized binaural signal processing and transducer array control are achieved.

These and further objects, features and advantages of the present invention will become apparent from the following description when taken in connection with the accompanying drawings which, for purposes of illustration only, shows several embodiments in accordance with the present invention.

BRIEF DESCRIPTION OF THE DRAWINGS

FIG. 1 schematically shows one embodiment of an intracochlear dual stimulation array;

FIG. 2 shows a detail of FIG. 1;

DETAILED DESCRIPTION OF THE INVENTION

Figure 3:
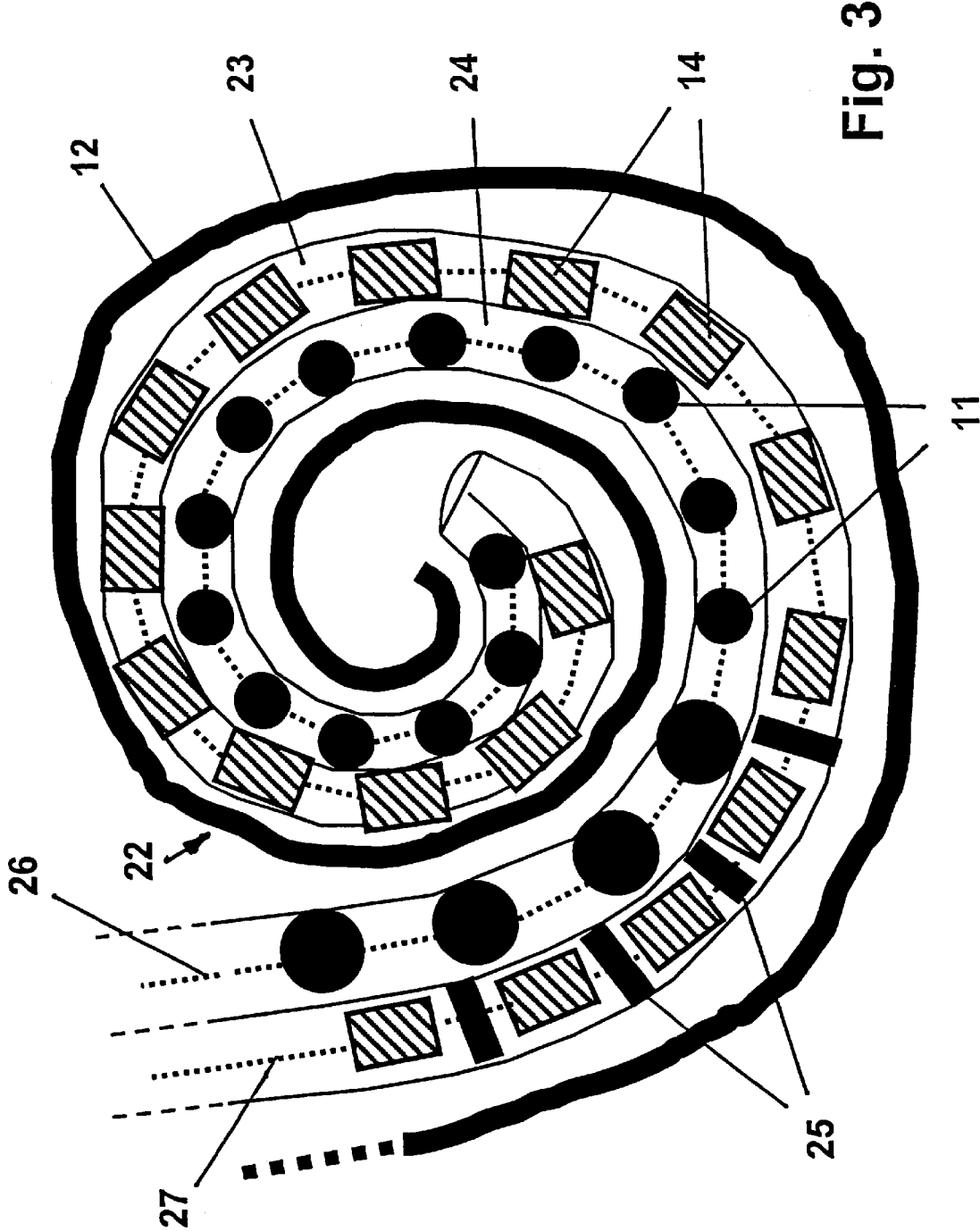
FIG. 3 schematically shows another embodiment of an intracochlear dual stimulation array.

FIG. 1 schematically shows an intracochlear dual stimulation array 10 with several cochlear implant electrodes 11 for direct electrical stimulation of the inner ear and several intracochlear electromechanical converters 14 for direct mechanical stimulation of the inner ear in a common mechanical carrier 13. Basically this array is built similarly to a multichannel intracochlear cochlear implant electrode array. The carrier 13 preferably comprises essentially a flexible silicone molded part of preferably circular cross section. The molded part is pushed through the oval window, the round window or an artificial opening of the cochlea 12 or into the fluid-filled inner ear spaces. The electromechanical converters 14 are shown schematically in FIG. 1 as cylindrical elements with likewise circular cross section. Within the carrier 13 there are electrical feeder lines to the cochlear implant electrodes 11 and converters 14; these feeder lines are not shown in detail.

The electromechanical converters 14 work preferably according to the principle of dynamic volume change as a result of dynamic surface enlargement or reduction according to a triggering electrical converter AC voltage signal. This dynamic change of volume or surface is shown schematically in FIG. 2. There the broken lines 15 and 16 show the minimum and the maximum volume. The required volume changes for a suitable equivalent acoustic pressure level of roughly 100 dB SPL are roughly $2 \cdot 10^{-4}$ microliters (U.S. Pat. No. 5,772,575).

The converters 14 are, for example, distributed equidistantly along the carrier 13 or at logarithmic distances according to the tonotopic location-frequency assignment along the basilar membrane of the inner ear. The total diameter of the converter electrode arrangement 10 is preferably in the range from 0.4 mm (apical area 18 as shown in FIG. 1) to 2.0 mm (basal area 19 as shown in FIG. 1). The total length of the stimulation array 10 is feasibly between 5 mm and 50 mm. The electromechanical converter elements 14 are preferably embedded in the carrier 13 for reasons of biocompatibility such that the electromechanical converter elements are completely surrounded by a thin layer of carrier material (not shown in FIG. 1). The carrier 13 of the stimulation array 10 comprises a biocompatible material which is biostable in the inner ear, preferably polymers such as the corresponding silicones.

The cochlear implant electrodes 11 are, as is known in cochlear implants, embedded in the carrier 13 or fixed in or on the carrier 13 such that a portion of the surface per stimulation electrode is in direct galvanic contact with the lymphatic fluid of the inner ear or directly with the neural structure to be stimulated. The cochlear implant electrodes 11 comprise all known biocompatible metals, especially pure platinum, preferably platinum-iridium alloys (preferably 90% Pt, 10% Ir), pure gold, gold alloys, tantalum, tantalum alloys, niobium, niobium alloys and high quality steels.

Advantageously, the electromechanical converters 14 and the cochlear implant electrodes 11 are arranged alternating in one another in the lengthwise direction of the carrier 13 so that mechanical wave propagation within the carrier between adjacent electromechanical converter elements is damped and thus locally concentrated mechanical stimulation per converter is achieved. A converter array feeder line is shown at 20.

FIG. 3 schematically shows another embodiment of an intracochlear dual stimulation array 22 with several electromechanical converters 14 and cochlear implant electrodes 11 in which in contrast to FIG. 1 the electromechanical converters 14 and the cochlear implant electrodes 11 are located in two separate carriers 23 and 24. As shown, the carriers 23, 24 can be mechanically connected to one another and are guided jointly into the cochlea 12 such that preferably the array with the cochlea implant electrodes 11 is oriented to the inside in order to lie as near as possible to the neural structures (modiolus) to be stimulated. The two carriers can also be completely mechanically independent of one another (not shown); the two carriers are then individually inserted simultaneously or in succession into the cochlea 12. Electrical feed lines for the cochlear implant electrodes 11 and the electromechanical converters 14 are indicated at 26 and 27.

Between the individual converters 14 of the electromechanical array mechanical attenuation elements 25 can be embedded in the carrier; the mechanical attenuation elements 25 minimize the mechanical wave propagation within the carrier 23 to the adjacent converter elements 14, similarly to as occurs in FIG. 1 by the cochlear implant electrodes 11 located in between. To achieve high attenuation values, the material of the attenuation elements 25 with a cross sectional geometry similar to that of the carrier 23 is preferably chosen such that there is a high mechanical impedance difference compared to the carrier material.

The electromechanical converters 14 can work according to any known electromechanical converter principle, specifically electromagnetic, electrodynamic, piezoelectric, magnetostrictive or dielectric (capacitive). The electromechanical converters 14 can be developed and produced using methods of microsystems engineering which allow high miniaturization and excellent reproducibility of the individual converters. These properties of production using microsystems engineering can be especially advantageous because as expected in the intended function of the converter array the phase synchronism of the individual electromechanical converters is important. One possible microsystems engineering structure of an individual converter is given in the patent literature of Ron Maynard (WO 99/03146).

The individual converters 14 are preferably triggered by an electronic preprocessing system which is described below such that by the respective choice of the spectral transmission range per converter, the vibratory amplitude and the phase angle of the converters to one another, in the overall actuator result of inner ear stimulation a traveling wave is formed on the basilar membrane which for the respective external sound event is as similar as possible to the traveling wave form which would result in an undamaged cochlear amplifier and thus with intact outer hair cells.

Figure 4:
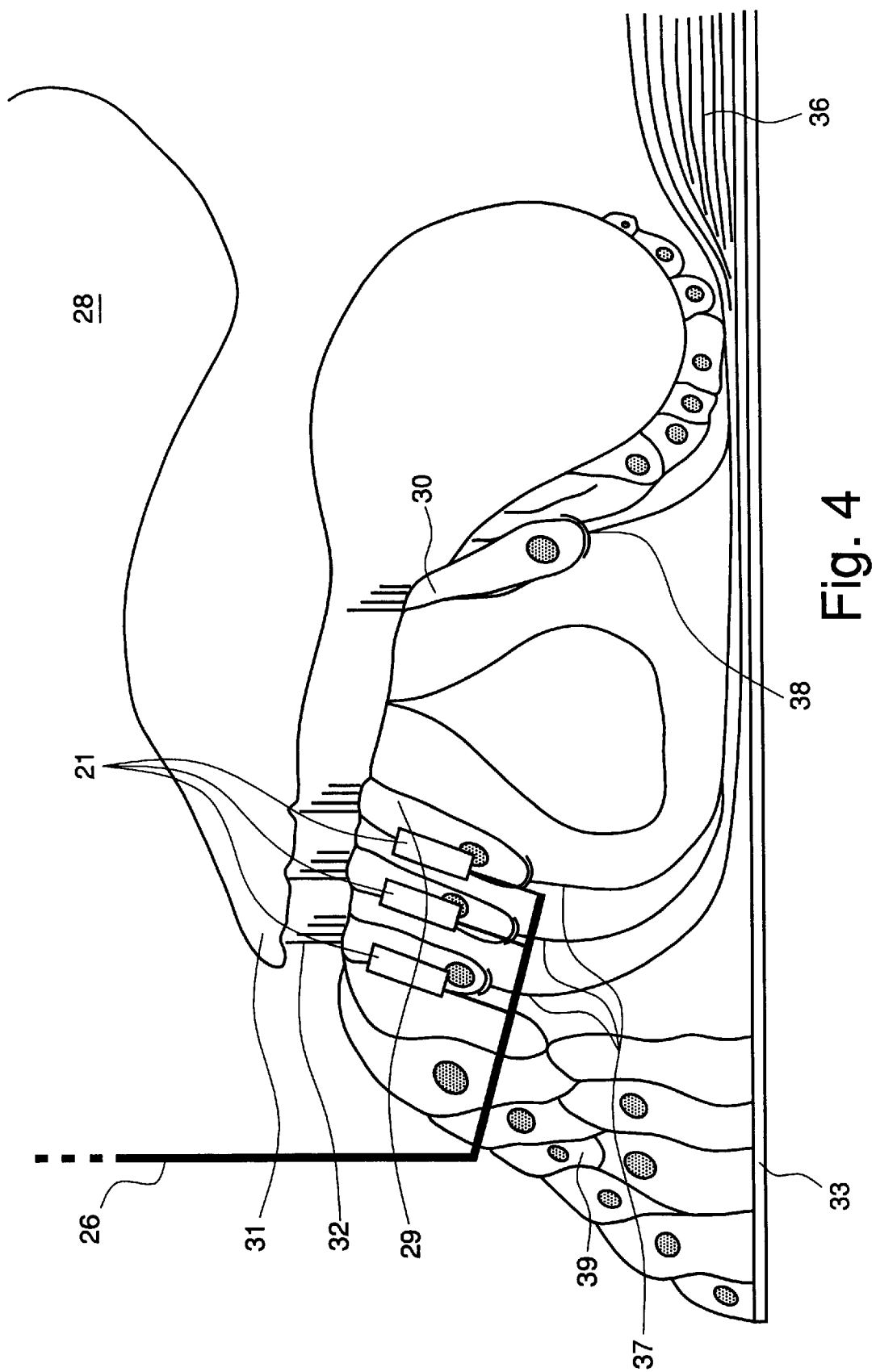
FIG. 4 shows schematically and in a representation enlarged compared to FIGS. 1 and 3, an arrangement in which for mechanical stimulation of the inner ear there are miniaturized intracochlear electrical stimulation electrodes which interact with the outer hair cells, FIG. 5 schematically shows one embodiment for the structure of the signal processing electronic module of an at least partially implantable hearing system, FIG. 6 schematically shows one embodiment for the structure of a completely implantable hearing system with an intracochlear dual stimulation array as shown in FIG. 1.

FIG. 4 shows on a larger scale part of the inner ear. Here, the inner ear space filled with intracochlear fluid is labeled 28, the external and internal hair cells are labeled 29 and 30, the tectorial membrane is labeled 31, the stereocilia 32, the basilar membrane 33, the auditory nerve 36, the efferent and afferent synapses 37 and 38, and the support cells are labeled 39. Instead of the electromechanical converters 14 for direct mechanical excitation of the inner ear as shown in FIGS. 1 to 3, in this embodiment, for indirect mechanical stimulation of the inner ear there are intracochlear hair cell stimulation electrodes 21 which in the implanted state are in the immediate vicinity of the outer hair cells 29. By means of the hair cell stimulation electrodes 21 the outer hair cells 29 are electrically stimulated artificially and the hair cells 29 react mechanically thereto with changes in length which mechanically stimulate the inner ear. With corresponding triggering by the processor system in the manner described below, as a result in turn provisions can be made for the formation of traveling waves on the basilar membrane 33 which for the respective external sound event approach as closely as possible the traveling wave form which would result in an undamaged cochlear amplifier.

Figure 5:
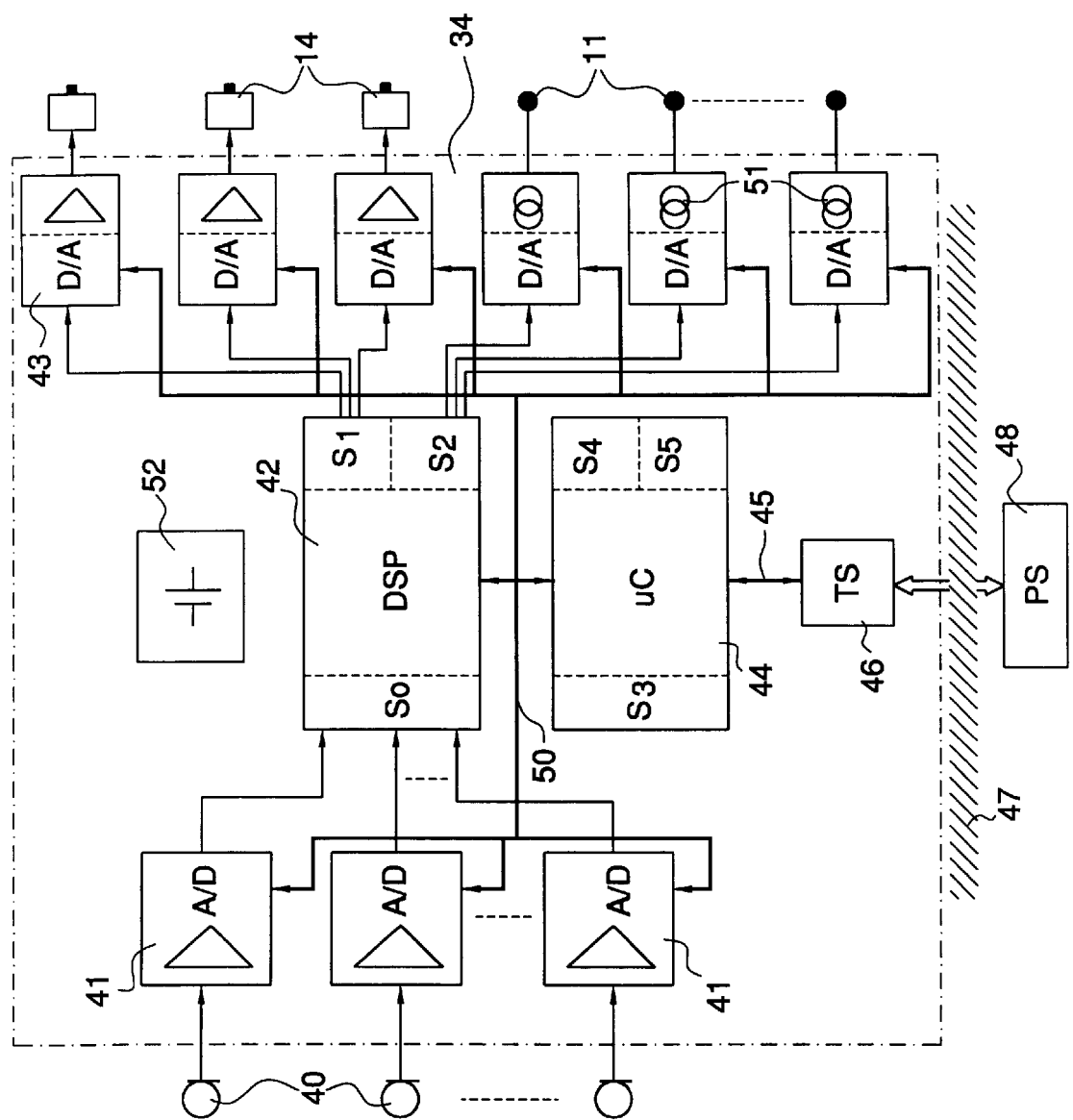

FIG. 5 shows the possible structure of the signal processing electronic module 34 of an at least partially implantable hearing system. The external acoustic signal is picked up via one or more acoustic sensors (microphones) 20 and is converted into electrical signals. The analog electrical sensor signals are routed to modules 41 in which the analog electrical sensor signals are preprocessed, especially pre-amplified, and converted into digital signals (A/D). This preprocessing can comprise, for example, in analog linear or nonlinear pre-amplification and filtering (for example, anti-aliasing filtration).

The digitized sensor signals are further processed in a digital signal processor 42 (DSP). The signal processor 42 contains a read-only-memory area $S_0$ which cannot be overwritten, in which the instructions and parameters necessary for "minimum operation" of the system are stored, and storage areas $S_1$ and $S_2$ in which the operating software of the intended function or functions of the implant system are stored. The rewriteable program storages $S_1$ and $S_2$ for storing the operating software can be based on EEPROM or on static RAM cells, and in the latter case provisions should be made for this RAM area to always be "buffered" by the power supply system within the implant.

The digital output signals of the signal processor 42 are converted in digital-analog converters (D/A) 43 into analog signals and amplified and then supplied to the cochlear implant electrodes 11 and the electromechanical converters 14 or the hair cell stimulating electrodes 21. The D/A converters 43 can optionally be omitted at least in part, if, for example, a pulse-width modulated, serial digital output signal of the signal processor 42 is transferred directly to the output converters 14 and/or there are digitally control power sources for the cochlear implant electrodes 11 and the hair cell stimulating electrodes 21.

The signal processor 42 executes the intended function of the hearing implant. This includes audio signal processing for rehabilitation of a hearing disorder and optionally also signal generation in the case of a system with additional tinnitus masker or noiser functions. Furthermore, the digital signal processor 42 contains software modules which undertake dual converter and stimulating electrode triggering such that the spectral, time, amplitude- and phase-referenced converter or stimulating electrode signal properties are configured such that optimum hearing success is achieved for the pertinent patient. It can be especially advantageous that with the intracochlear dual converter array not only one, but several electromechanical converters are directly implanted in the fluid-filled space of the inner ear (scale tympani or scala vestibuli) and the several electromechanical converters vibrationally stimulate the fluid-filled inner ear spaces in locally varied areas along the basilar membrane, and thus, lead to a hearing impression. In doing so, the individual electromechanical converters are advantageously triggered by an electronic preprocessing system such that by the respective choice of the spectral transmission range per converter, the vibratory amplitude and the phase angle of the converters to one another, in the overall actuator result of inner ear stimulation a traveling wave is formed on the basilar membrane which for the respective external sound event is as similar as possible to the traveling wave form which would result in an undamaged cochlear amplifier and thus with intact outer hair cells.

These software modules can be designed to be static and dynamic. A static design is defined as the software modules, based on scientific findings, being filed once in the program storage of the signal processor 42 and remaining unchanged. Dynamic means that these software modules are "able to learn", in order to approach as optimally as possible the desired hearing result in a time iterative manner. This means that the software modules can be designed to be adaptive, and parameter matching is accomplished by training by the implant wearer, and optionally, other aids such as rehabilitation programs. Furthermore, a software module can be contained which approximates hearing supply as optimum as possible based on an adaptive neural network. Training of this neural network can take place again by the implant wearer and/or using other external aids.

One method for simulation of a "healthy" cochlear amplifier as optimum as possible by multichannel electromechanical stimulation by the electromechanical converter array can be the software implementation of the principle of "Time-Reversed Acoustics (TRA) (Fink, M: Time-Reversed Acoustics" Scientific American 281:5 (1999), pp. 67–73). Triggering of the electromechanical converter elements 14 takes place by TRA such that locally limited areas of the cochlea are mechanically stimulated. While in conventional applications of TRA the registration of the distributed sound event and the transmission of the time-reversed signal can take place in the same preparation, these two steps are separated in this case. The distributed events can be determined intracochlearly, for example, in a suitable animal model; then, the time-reversed stimuli in this application of a hearing system are applied to humans, optionally with parameter matching to the altered geometry of the human cochlea.

In order to also postoperatively implement the described software-based algorithms for an as optimum as possible dual stimulation of the damaged hearing especially in a total implant, the system shown in FIG. 2 contains a further microprocessor module, for example, a microcontroller (μC) 44 with the associated storages ($S_3$, $S_4$, $S_5$). The storage $S_3$ is a rewriteable storage in which an operating program for the microcontroller 44 is stored. Especially the operating software portions of the implant management system (for example, administration, monitoring and telemetry functions) can be stored in the storage areas $S_4$ and $S_5$. Storages $S_1$ and/or $S_2$ and/or $S_4$ and/or $S_5$ can also store patient-specific, for example audiological adaptation parameters which can be altered from the outside.

On the one hand, the microcontroller 44 communicates via a bidirectional data bus 45 and a telemetry system (TS) 46 wirelessly (for example, via inductive coupling) through the closed skin indicated at 47 with an external programming system (PS) 48. The programming system 48 can be a PC-based system with corresponding programming, processing, display and administration software. Via this telemetry interface the operating software of the implant system which is to be changed or completely replaced is transmitted and at first buffered in the storage area $S_4$ and/or $S_5$ of the microcontroller 44. Thus, for example, simple verification of software transmission can be accomplished by a reading process via the telemetry interface before the operating software or the corresponding signal processing portions of this software are transmitted into the program storage areas $S_1$ and $S_2$ of the digital signal processor 42 via a data bus 50. Furthermore, the working program for the microcontroller 44 can be changed or replaced in whole or in part via the telemetry interface using the external unit 48.

On the other hand, the microcontroller 44 controls, via the bidirectional data bus 50, the signal processor 42, the A/D converter 41 for sensor preprocessing and the D/A converter 43 for triggering the electromechanical converters 14 and for triggering the cochlear implant electrodes 11 or the hair cell stimulating electrodes 21 within the implant. Via the data bus 50, program parts or entire software modules can also be transferred between the outside world, i.e., an external unit, the microcontroller 44 and the signal processor 42.

In the fully implanted embodiment, the implant system also contains a primary or secondary battery cell 52 which supplies the individual modules with electrical operating energy.

If, instead of the electromechanical converters 14 in conjunction with the circuit of FIG. 5, there are hair cell stimulating electrodes 21 for indirect mechanical inner ear stimulation, preferably power sources according to the power sources 51 shown in FIG. 5 for the cochlear implant electrodes 11 are connected upstream of these electrodes 21.

Figure 6:
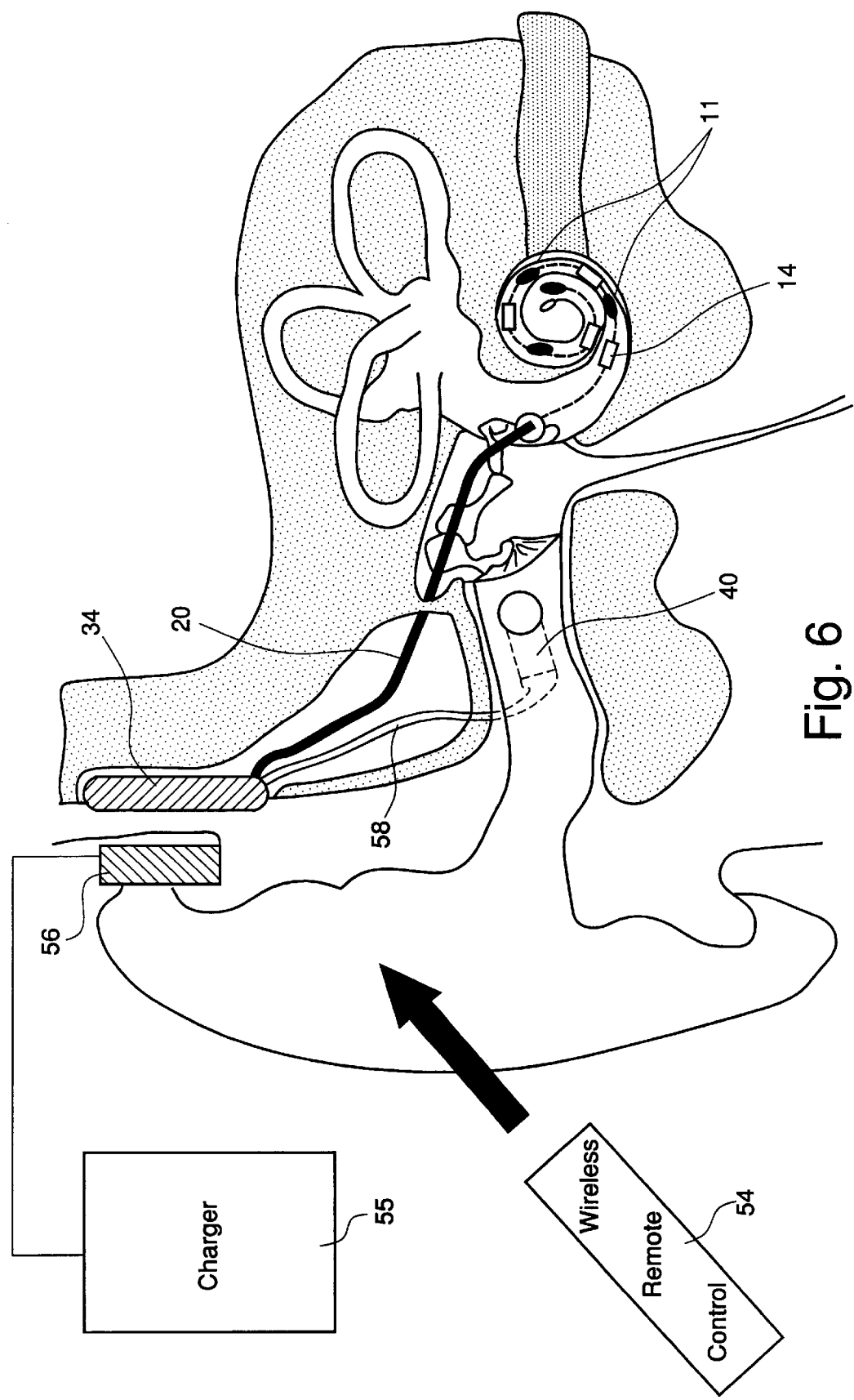

FIG. 6 schematically shows the structure of a completely implantable hearing system with an intracochlear stimulation array 10 as shown in FIG. 1, a signal processing electronic module 34 as shown in FIG. 5 and an implantable microphone 40. There can also be several microphones for picking up the acoustic signal and converting the acoustic signal into the corresponding electrical signals. A wireless remote control 54 is used to control the implant functions by the implant wearer. Furthermore, there is a charging system with a charger 55 for wireless transcutaneous recharging of an secondary battery located in the implant for power supply of the hearing system, for example of the battery 52 in FIG. 5.

In this hearing system, instead of the stimulation array 10 as shown in FIG. 1, the stimulation array 22 as shown in FIG. 2 or an arrangement with a combination of cochlear implant electrodes 11 and hair cell stimulating electrodes 21 as shown in FIG. 4 can be used.

The microphone 40 can advantageously be built in the manner known from published European Patent Application EP 0 831 673 A2 and can be provided with a microphone capsule which is accommodated hermetically sealed on all sides within a housing, and with an electrical feed-through wire connector for routing at least one electrical connection from within the housing to outside thereof, wherein the housing has at least two legs, which are arranged at an angle relative to one another, a first of said legs containing the microphone capsule and being provided with a sound inlet membrane, and a second of said legs containing the electrical feed-through wire connector and being set back relative to the plane of the sound inlet membrane, and wherein the geometry of the microphone housing is chosen such that when the microphone is implanted in the mastoid cavity the leg which contains the sound inlet membrane projects from the mastoid into an artificial hole in the posterior bony wall of the auditory canal and the sound inlet membrane touches the skin of the wall of the auditory canal. To fix the implanted microphone 20, there can preferably be a fixation element of the type known from U.S. Pat. No. 5,999,632 which has a sleeve, a cylindrical housing part of which surrounds the leg which contains the sound inlet membrane, wherein the sleeve is provided with projecting, elastic flange parts which can be placed against the side of the wall of the auditory canal facing the skin of the auditory canal. The fixation element preferably comprises a holding device which, before implantation, maintains the flange parts mentioned above, against the elastic restoration force of the flange parts, in a bent position which allows insertion through the hole of the wall of the auditory canal.

The charging system also includes a charging coil 56 which is connected to the output of the charger 55 and which preferably in the manner known from U.S. Pat. No. 5,279,292 forms part of the transmitting serial resonant circuit which can be inductively coupled to the receiving serial resonant circuit which is not shown. The receiving serial resonant circuit can be part of the electronic module 34 in the embodiment as shown in FIG. 5 and according to U.S. Pat. No. 5,279,292 can form a constant current source for the battery 52 (FIG. 5). Here, the receiving serial resonant circuit is in the battery charging circuit which depending on the respective phase of the charging current flowing in the charging circuit is closed via one branch or the other of a full wave rectifier bridge.

The electronic module 34 is connected in the arrangement as shown in FIG. 6 via a microphone line 58 to the microphone 40 and via the converter array feed line 20 to the intracochlear stimulation array 10.

Figure 7:
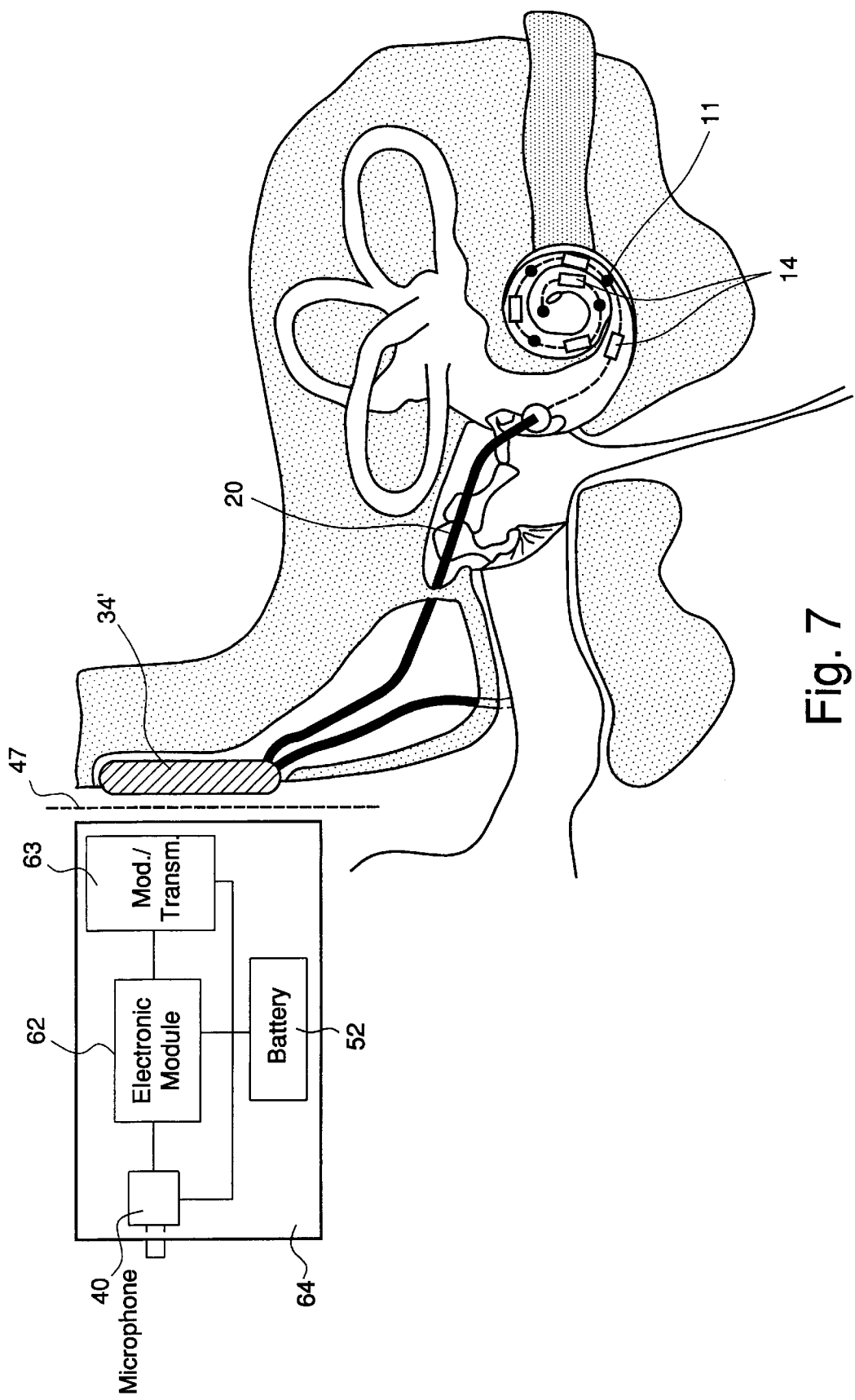
FIG. 7 schematically shows one embodiment for the structure of a partially implantable hearing system with an intracochlear dual stimulation array as shown in FIG. 1.

FIG. 7 schematically shows the structure of a partially implantable hearing system with an intracochlear stimulation array 10 as shown in FIG. 1. This partially implantable system contains a microphone 40, an electronic module 62 for electronic signal processing for the most part according to FIG. 5 (but without the telemetry system 46), the power supply 52 and a modulator/transmitter unit 63 in an external module 64 which is to be worn externally on the body, preferably on the head over the implant. As in the known partial implants, the implant is passive in terms of energy. Its electronic module 34' (without the battery 52) receives its operating energy and converter control data via the modulator/transmitter unit 63 in the external part 64. In this partially implantable hearing system there can also be a stimulation array as shown in FIG. 2 or stimulation electrodes as shown in FIG. 4 and that a binaural application similarly to the embodiments explained below is possible.

Figure 8:
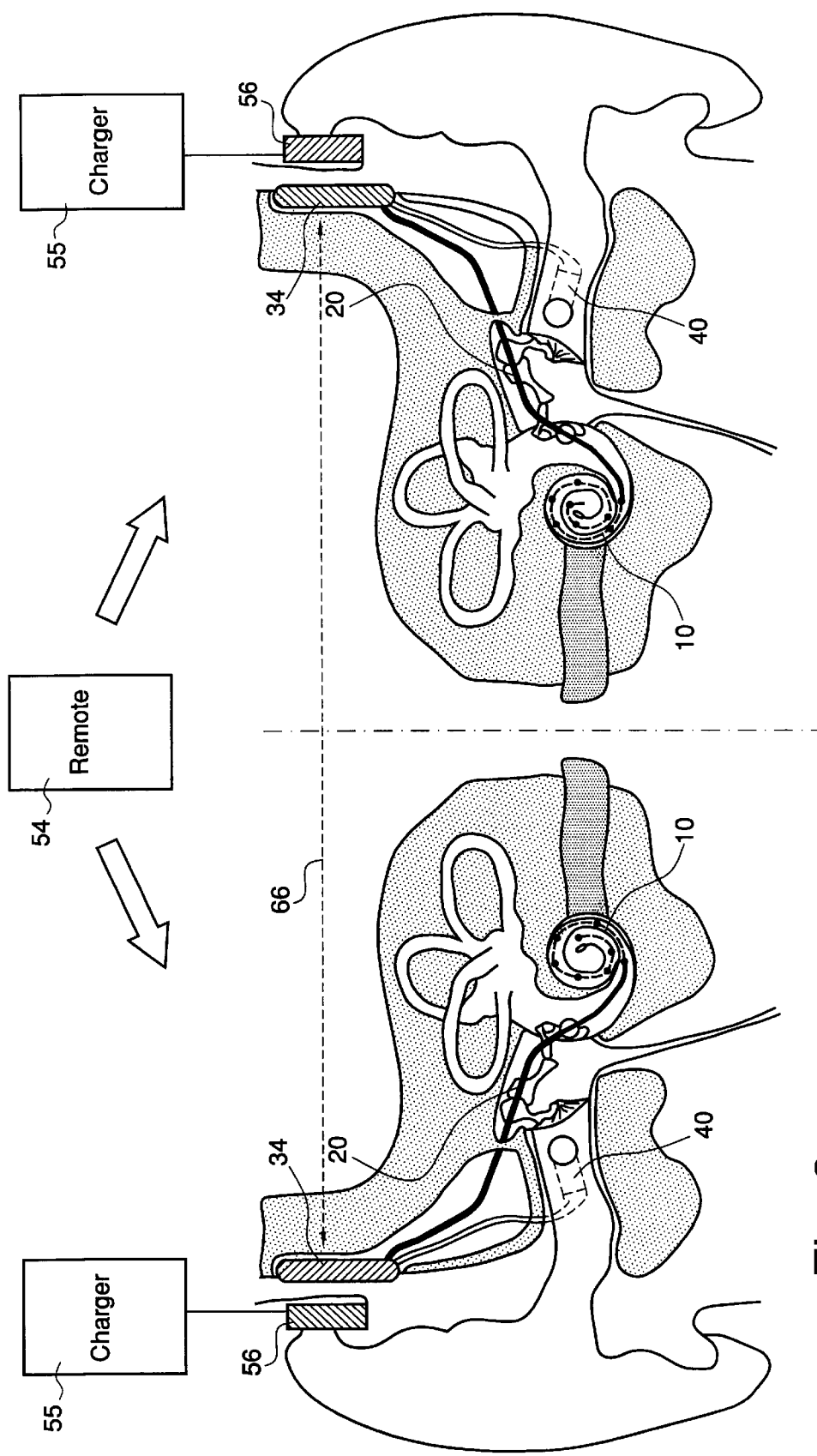
FIG. 8 shows a binaural application of a hearing implant as shown in FIG. 6 in which the signal processing modules communicate with one another via a wired implantable line connection.

FIG. 8 shows a binaural application of a fully implantable hearing implant of the type explained using FIGS. 1 to 6. Here, as in the following figures, the intracochlear dual stimulation array 10 (or 22) is shown only schematically without details. The signal processing modules 34 of the two systems communicate with one another via a wired implantable line connection 66 such that optimum binaural sensor signal processing and stimulation array triggering in the two implanted inner ears are achieved. Furthermore, here, there are also transcutaneous charging devices 55, 56 for the case of implant-side secondary energy storage elements (batteries 52) and a wireless remote control 54 which synchronously controls the two electronic modules 34 for use by the implant wearer.

Figure 9:
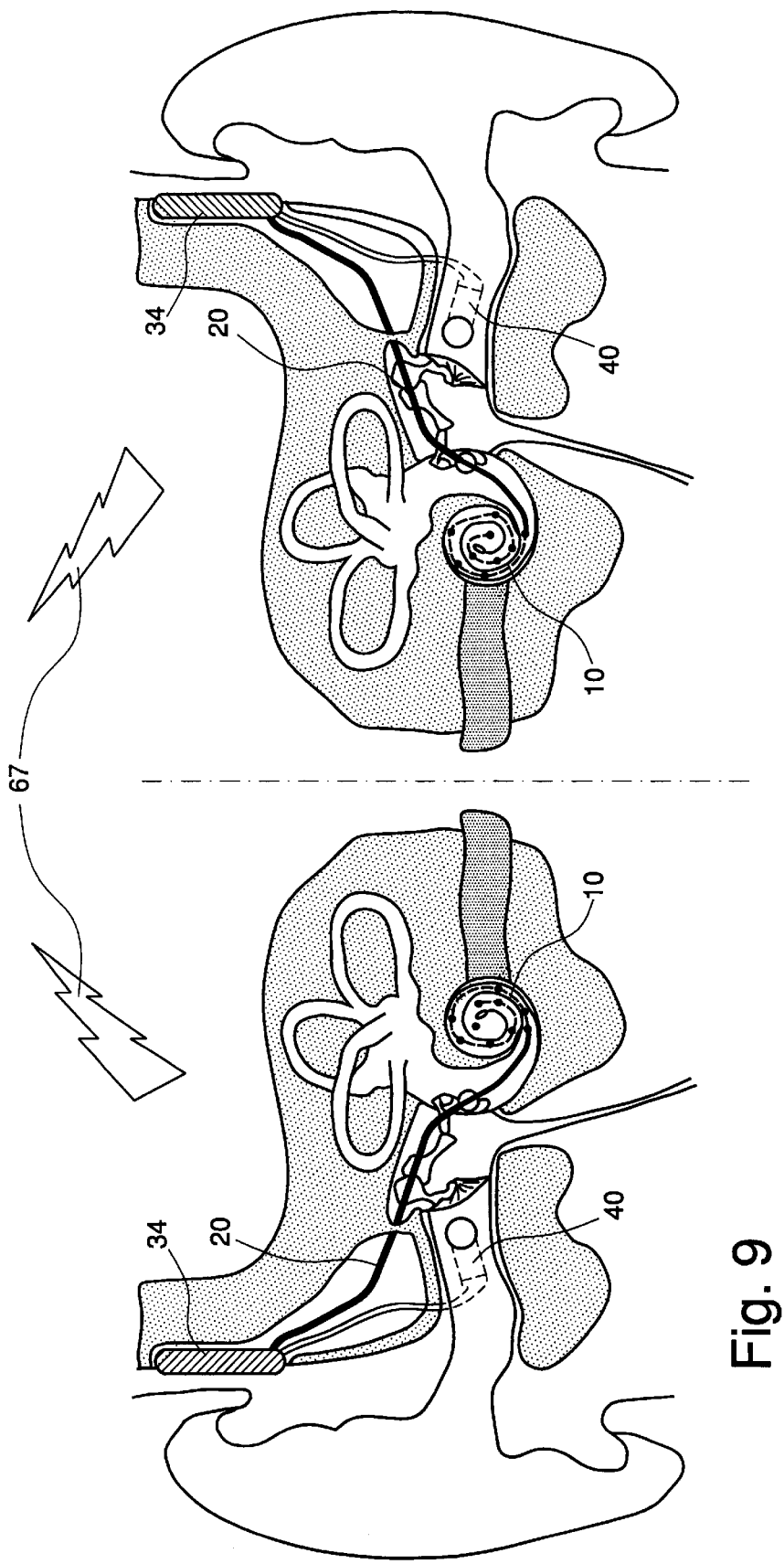
FIG. 9 shows a binaural application of a hearing implant as shown in FIG. 6 in which the signal processing modules communicate with one another via a wireless connection.

FIG. 9 shows the binaural application of a hearing implant in which the signal processing modules 34 communicate with one another via a wireless connection (for example a bidirectional high frequency section indicated at 67) such that optimum binaural sensor signal processing and stimulation array triggering in the two implanted inner ears are achieved. Here there are also transcutaneous charging devices 55, 56 for the case of implant-side secondary energy storage elements (batteries 52) and a wireless remote control 54 for use by the implant wearer which synchronously controls the two electronic modules 34, but as in the two following embodiments described below and illustrated in FIGS. 10 and 11, not shown.

Figure 10:
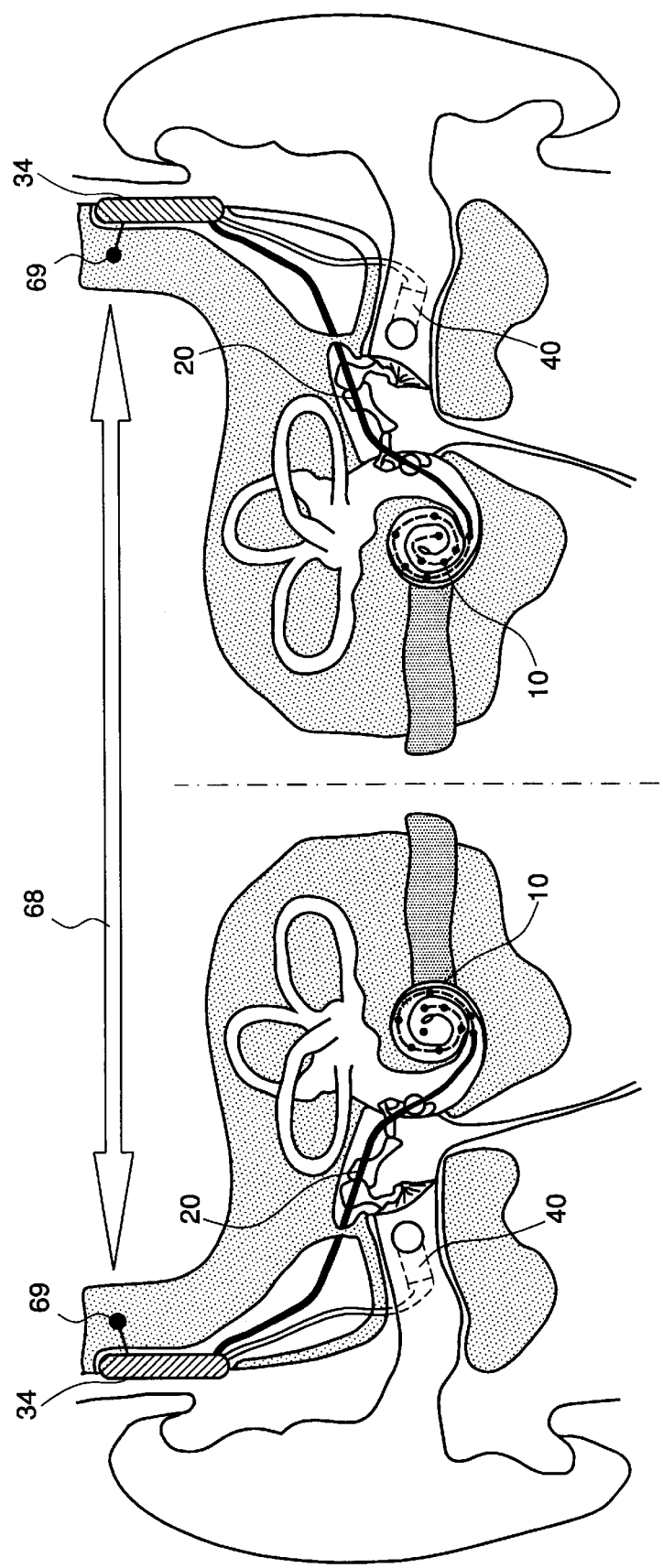
FIG. 10 shows a binaural application of a hearing implant as shown in FIG. 6 in which the signal processing modules communicate with one another via a solid borne sound-coupled ultrasonic section.

The binaural execution of the hearing implant as shown in FIG. 10 differs from that of FIG. 9 only in that for wireless communication between the signal processing modules 34 of the two system units there is a solid borne sound-coupled ultrasonic section 68 with ultrasonic couplers 69. Here, for example, the digital, bidirectional information is preferably amplitude modulated or frequency modulated onto a carrier in the ultrasonic range. The ultrasonic couplers 69 can be, as shown in FIG. 10, ultrasonic transmitters and receivers which are locally separated from the electronic module 34, which are connected via electrical lines, and which are preferably coupled securely in the mastoid area to the skull bone. The ultrasonic couplers however can also be integrated in the electronic modules 34 (not shown) when the electronic modules are implanted in the mastoid area such that ultrasonic solid-borne transmission can take place through the skull bone.

Figure 11:
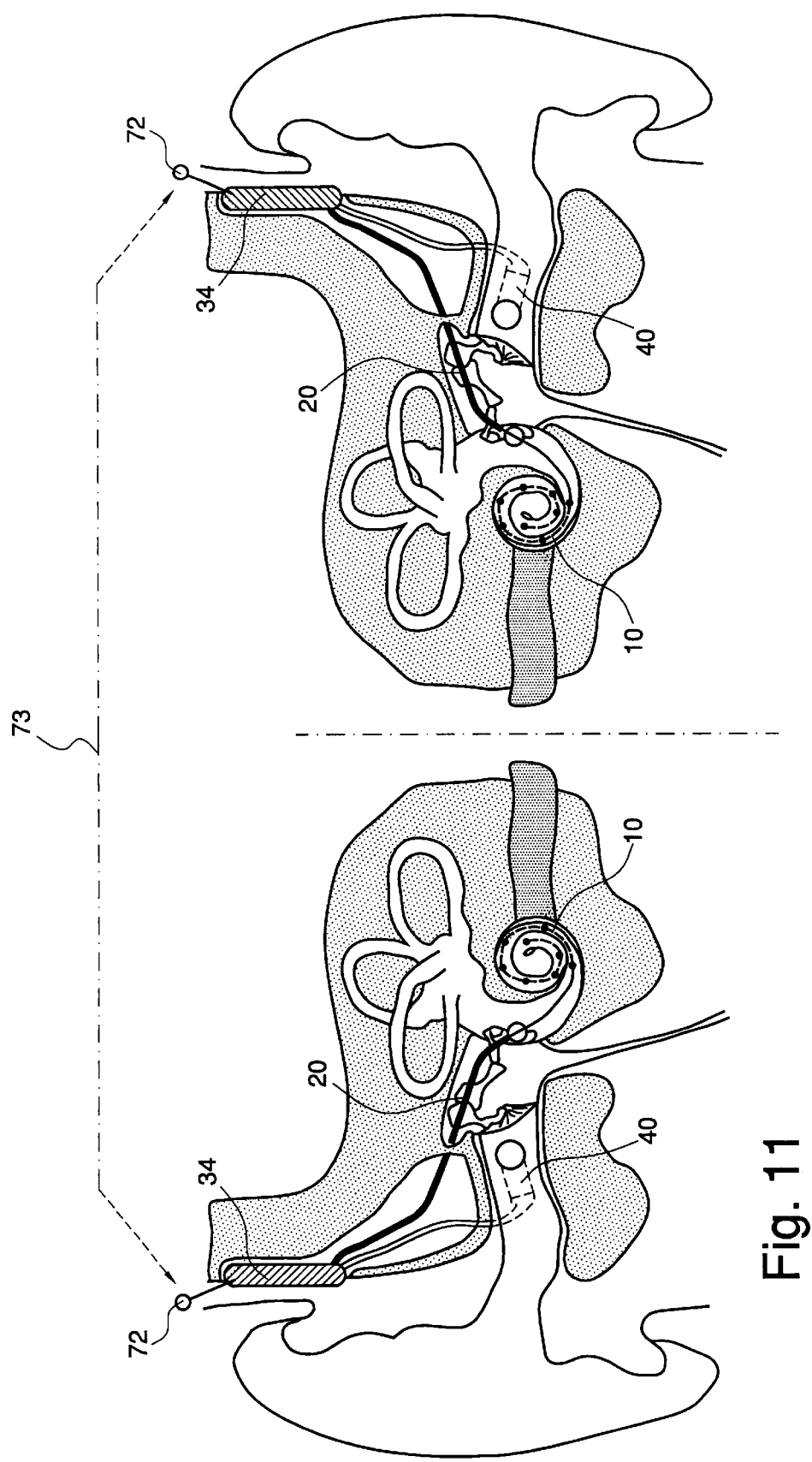
FIG. 11 shows a binaural application of a hearing implant as shown in FIG. 6 in which the signal processing modules communicate with one another via a transmission section which includes the tissue of the implant wearer.

A further modified embodiment of a binaurally formed hearing implant is shown in FIG. 11. In this embodiment, in contrast to the embodiments of FIGS. 8 to 10, for example, the digital, bidirectional information is preferably amplitude modulated or frequency modulated on the implant side onto a carrier and applied to the implanted electrodes 72 which are part of a data transmission section 73 which leads through the body tissue of the implant wearer. Thus a modulated tissue current is obtained which in the known manner (U.S. Pat. No. 5,113,859) provides for the desired communication between the signal processing modules 34 of the two system units.

It goes without saying that a partially implantable system can also be binaurally applied and that then provisions can be made for communication between the two system units preferably according to the embodiments of binaural applications of fully implantable systems which are shown in FIGS. 8 to 11.

While several embodiments in accordance with the present invention have been shown and described, it is understood that the invention is not limited thereto, and is susceptible to numerous changes and modifications as known to those skilled in the art. Therefore, this invention is not limited to the details shown and described herein, and includes all such changes and modifications as encompassed by the scope of the appended claims.

We claim:

1. An at least partially implantable system for rehabilitation of a hearing disorder comprising:

at least one acoustic sensor for picking up an acoustic sensor signal and converting the acoustic sensor signal into corresponding electrical signals, an electronic signal processing unit for audio signal processing and amplification, an electrical power supply unit which supplies individual components of the system with energy, and an output-side actuator stimulation arrangement, wherein the actuator stimulation arrangement comprises a dual intracochlear, stimulator arrangement with at least one intracochlear stimulator element for at least indirect electromechanical stimulation of a damaged inner ear and at least one intracochlear electrically acting stimulation electrode arrangement with at least one cochlear implant electrode for electrical stimulation of the damaged inner ear.

2. The system as claimed in claim 1, wherein the stimulator arrangement has at least one intracochlear electromechanical converter for direct mechanical stimulation of the inner ear.

3. The system as claimed in claim 1, wherein the stimulator arrangement has at least one intracochlear hair cell stimulating electrode for indirect mechanical stimulation of the inner ear by electrical stimulation of outer hair cells.

4. The system as claimed in claim 1, wherein the actuator stimulation arrangement comprises an intracochlear array with several stimulator elements for mechanical stimulation of the inner ear.

5. The system as claimed in claim 3, wherein the at least one hair cell stimulation electrode is adapted to rest in an immediate vicinity of the outer hair cells for indirect mechanical stimulation of the inner ear, in an implanted state.

6. The system as claimed in claim 1, wherein the at least one cochlear implant electrode is attached to a carrier is adapted to be in direct galvanic contact with one of a lymphatic fluid of the inner ear and a neural structure to be stimulated for electrical stimulation of the inner ear, in an implanted state.

7. The system as claimed in claim 2, wherein a common carrier is provided for the at least one cochlear implant electrode and the at least one electromechanical converter.

8. The system as claimed in claim 7, wherein the at least one electromechanical converter and the at least one cochlear implant electrode comprise a plurality of electromechanical converters and cochlear implant electrodes arranged in an alternating sequence along the carrier.

9. The system as claimed in claim 2, wherein a first carrier is provided for the at least one cochlear implant electrode and a second carrier is provided for the at least one electromechanical converter.

10. The system as claimed in claim 9, wherein the first carrier for the at least one cochlear implant electrode is adapted to be closer to the neural structures of the cochlea than the second carrier in an implanted state.

11. The system as claimed in claim 7, wherein the total diameter of the dual intracochlear arrangement is in the range from 0.4 mm to 2.0 mm.

12. The system as claimed in claim 7, wherein the total length of the dual intracochlear arrangement is between 5 mm and 50 mm.

13. The system as claimed in claim 7, wherein the carrier comprises a biocompatible material which is bio-stable in the inner ear.

14. The system as claimed in claim 13, wherein the biocompatible material is a polymer.

15. The system as claimed in claim 13, wherein the biocompatible material is a silicone.

16. The system as claimed in claim 7, wherein the at least one electromechanical converter is embedded in the carrier such that the at least one electromechanical converter is completely surrounded by a thin layer of a carrier material.

17. The system as claimed in claim 7, wherein the at least one electromechanical converter comprises a plurality of electromechanical converters; and wherein mechanical attenuation elements are embedded in the carrier between the electromechanical converters for minimizing mechanical wave propagation within the carrier between adjacent electromechanical converters.

18. The system as claimed in claim 17, wherein an attenuation element material of the attenuation elements has a first cross sectional geometry similar to a second cross sectional geometry of the carrier and the attenuation element material has a high mechanical impedance difference as compared to that of the carrier material in order to achieve high attenuation values.

19. The system as claimed in claim 18, wherein the attenuation elements are formed by cochlear implant electrodes.

20. The system as claimed in claim 2, wherein the at least one electromechanical converter adapted to operate according to one of electromagnetic, electrodynamic, piezoelectric, magnetostrictive and capacitive principles.

21. The system as claimed in claim 20, wherein the at least one electromechanical converter is a piezoelectric converter made of one of lead zirconate titanate and polyvinylidene fluoride.

22. The system as claimed in claim 2, wherein the at least one electromechanical converter is made with passive material partners adapted to operate on a geometrical shape transformation principle which produces maximum deflection with minimum electric power consumption at converter voltage.

23. The system as claimed in claim 22, wherein the geometrical shape transformation principle is one of the bimorph principle, the unimorph principle and the heteromorph principle.

24. The system as claimed in claim 4, wherein the several stimulator elements are adapted distributed equidistantly along a basilar membrane of the inner ear in an implanted state for mechanical stimulation of the inner ear.

25. The system as claimed in claim 4, wherein the several stimulator elements are adapted to be distributed at logarithmic distances according to a tonotopic frequency-location assignment along a basilar membrane of the inner ear in an implanted state for mechanical stimulation of the inner ear.

26. The system as claimed in claim 24, wherein 20 to 24 stimulator elements are provided according to psychoacoustic critical bands in a tonotopic arrangement of stimulator elements for mechanical stimulation of the inner ear.

27. The system as claimed in claim 26, wherein the stimulator elements are arranged in groups of stimulator elements.

28. The system as claimed in claim 2, wherein the at least one electromechanical converter has a transmission range from about 100 Hz to about 10 kHz.

29. The system as claimed in claim 2, wherein the at least one electromechanical converter is tuned to have a first mechanical resonant frequency at an upper end of a desired transmission frequency range.

30. The system as claimed in claim 29, wherein the desired transmission frequency range is about 8 kHz to about 10 kHz.

31. The system as claimed in claim 2, wherein the at least one electromechanical converter is hermetically sealed.

32. The system as claimed in claim 1, wherein the at least one cochlear implant electrode is produced from a material selected from the group consisting of platinum, platinum-iridium alloy, gold, gold alloy, tantalum, tantalum alloy, niobium, niobium alloy, and high quality steel.

33. The system as claimed in claim 32, wherein the platinum-iridium alloy is about 90% platinum and about 10% iridium.

34. The system as claimed in claim 5, wherein the at least one hair stimulation electrode is produced from a material selected from the group consisting of platinum, platinum-iridium alloy, gold, gold alloy, tantalum, tantalum alloy, niobium, niobium alloy, and high quality steel.

35. The system as claimed in claim 34, wherein the platinum-iridium alloy is about 90% platinum and about 10% iridium.

36. The system as claimed in claim 1, wherein the electronic signal processing unit has a preprocessing arrangement for at least one of pre-amplification and filtering, and for analog-digital conversion of the acoustic sensor signal.

37. The system as claimed in claim 36, wherein the preprocessing arrangement comprises anti-aliasing filters.

38. The system as claimed in claim 1, wherein a plurality of acoustic sensors are provided and each of the plurality of acoustic sensors is upstream of an analog-digital converter.

39. The system as claimed in claim 1, wherein the electronic signal processing unit contains software modules which enable masking of tinnitus parallel to operation of the hearing aid.

40. The system as claimed in claim 1, wherein the electronic signal processing unit has a digital signal processor for processing analog-digital-converted acoustic sensor signals, and the analog-digital-converted acoustic sensor signals; and wherein a preprocessing arrangement is provided for preprocessing the analog-digital-converted acoustic sensor signals for generation of digital signals for tinnitus masking.

41. The system as claimed in claim 1, wherein at least one digital-analog converter is connected upstream of the actuator stimulation arrangement.

42. The system as claimed in claim 41, wherein a digital-analog converter is provided upstream of the at least one stimulator element for mechanical stimulation of the inner ear and the at least one cochlear implant electrode for electrical stimulation of the inner ear.

43. The system as claimed in claim 1, wherein the electronic signal processing unit contains software modules which trigger the at least one stimulator element for mechanical stimulation of the inner ear by electrical signals having at least one of spectral, time, amplitude-referenced and phase-referenced properties for producing a traveling wave on a basilar membrane of a damaged inner ear in an implanted state which is as near as possible to that of healthy hearing.

44. The system as claimed in claim 43, wherein the electronic signal processing unit has a digital signal processor, and wherein the software modules are static being unchangeable once filed in a program storage of the digital signal processor.

45. The system as claimed in claim 1, wherein a PC-based wireless telemetry means for transmission of data between an implanted part of the system and an external unit is provided.

46. The system as claimed in claim 45, wherein the external unit is an external programming system.

47. The system as claimed in claim 43, wherein the software modules are dynamic.

48. The system as claimed in claim 47, wherein the software modules are adaptive, parameter matching in an implanted state by at least one of training conducted by an implant wearer and modification by an external aid.

49. The system as claimed in claim 1, wherein the electronic signal processing unit contains a software module for optimal simulation of a healthy cochlear amplifier based on an adaptive neural network.

50. The system as claimed in claim 49, wherein the adaptive neural network is adaptive by at least one of training conducted by an implant wearer and modification by an external aid.

51. The system as claimed in claim 49, wherein the electronic signal processing unit is adapted to produce a time-reversed acoustics principle triggering, of the stimulator elements for mechanical stimulation of the inner ear such that locally limited areas of the cochlea are mechanically stimulated, in an implanted state in the adaptive neural network for simulation of a healthy cochlear amplifier.

52. The system as claimed in claim 45, wherein the electronic signal processing unit has a digital signal processor and wherein a rewritable implantable storage arrangement is assigned to the digital signal processor for accommodating and reproducing an operating program in a manner enabling at least parts of the operating program to be replaced or changed by data transmitted from the external unit via the telemetry means.

53. The system as claimed in claim 52, wherein a buffer storage arrangement is provided in which data transmitted from the external unit via the telemetry means can be buffered before the data are relayed to the digital signal processor.

54. The system as claimed in claim 53, wherein a checking logic is providing for checking the data stored in the buffer storage arrangement before the data are relayed to the digital signal processor.

55. The system as claimed in claim 40, wherein a microprocessor module is provided for control of one of an analog-digital converter, a digital-analog converter, and the digital signal processor via a data bus within the implant.

56. The system as claimed in claim 55, wherein the microprocessor module is a microcontroller.

57. The system as claimed in claim 54, wherein the checking logic and the buffer storage arrangement are implemented in a microprocessor module.

58. The system as claimed in claim 55, wherein at least a part of a software module can be transferred between an external unit, the microprocessor module, and the digital signal processor via the data bus and a PC-based wireless telemetry means.

59. The system as claimed in claim 55, wherein an implantable storage arrangement for storing a working program for the microprocessor module is assigned to the microprocessor module, and at least a part of a working program for the microprocessor module can be changed or replaced by data transferred from an external unit via a PC-based wireless telemetry means.

60. The system as claimed in claim 52, wherein at least two storage areas are provided for holding and reproducing at least the operating program of the digital signal processor.

61. The system as claimed in claim 54, wherein the buffer storage arrangement has at least two storage areas for holding and reproducing data transferred from an external unit via the telemetry means.

62. The system as claimed in claim 40, wherein a preprogrammed read-only memory area is assigned to the digital signal processor.

63. The system as claimed in claim 40, wherein a PC-based telemetry means is provided for transmission of operating parameters between an implanted part of the system and an external unit.

64. The system as claimed in claim 1, wherein the system is an implantable system having an implantable unit that comprises the at least one acoustic sensor, and a rechargeable electrical storage element of the electric power supply unit; and wherein a wireless, transcutaneous charging device is provided for charging of the storage element.

65. The system as claimed in claim 64, wherein a wireless remote control is provided for enabling controlling of implant functions by an implant wearer.

66. The system as claimed in claim 1, wherein the system is a partially implantable system comprising a modulator/transmitter unit contained in an external module which is externally wearable on a body of an implant wearer; wherein an implantable part of the partially implantable system is passive in terms of energy; and wherein the implantable part of the partially implantable system receives operating energy and control data for mechanical and electrical inner ear stimulation via the modulator/transmitter unit in the external module.

67. The system as claimed in claim 1, wherein the system is a binaural system having two system units for rehabilitation of a hearing disorder of both ears, a respective system unit being provided for each of the ears of a user.

68. The system as claimed in claim 67, wherein the two system units are essentially identical to one another.

69. The system as claimed in claim 67, wherein one of the two system units is a master unit and another of the system units is a slave unit which is controlled by the master unit.

70. The system as claimed in claim 67, wherein a wired implantable line connection is provided for enabling one of the electronic signal processing unit of one of the system units to communicate with the electronic signal processing units of the other system unit to optimize binaural signal processing and converter array triggering.

71. The system as claimed in claim 67, wherein a wireless connection is provided for enabling communication between the electronic signal processing units of the two system units to optimize binaural signal processing and converter array triggering.

72. The system as claimed in claim 71, wherein the wireless connection is a bidirectional high frequency section.

73. The system as claimed in claim 67, wherein ultrasonic couplers are provided for enabling the electronic signal processing units of the two system units to communicate with one another via a solid borne sound-coupled ultrasonic section to optimize binaural signal processing and converter array triggering.

74. The system as claimed in claim 67, wherein the electronic signal processing units are connected to implantable electrodes and the implantable electrodes, in an implanted state are adapted to enable data transmission through body tissue of an implant wearer for communication of the electronic signal processing units of the two system units.

75. The system as claimed in claim 1, wherein the at least one stimulator element for mechanical stimulation of the inner ear and the at least one stimulation electrode for electrical stimulation of the inner ear are selectively operable.

76. The system as claimed in claim 1, wherein the at least one stimulator element for mechanical stimulation of the inner ear and the at least one stimulation electrode for electrical stimulation of the inner ear are simultaneously operable.

* * * * *